(12) United States Patent
Xu et al.

(10) Patent No.: US 11,179,385 B2
(45) Date of Patent: Nov. 23, 2021

(54) RESIQUIMOD TOPICAL AND INJECTABLE COMPOSITIONS FOR THE TREATMENT OF NEOPLASTIC SKIN CONDITIONS

(71) Applicant: THE TRUSTEES OF THE UNIVERSITY OF PENNSYLVANIA, Philadelphia, PA (US)

(72) Inventors: Xiaowei Xu, Monmouth Drive, NJ (US); Shujing Liu, Philadelphia, PA (US); Alain Rook, Wynnewood, PA (US); Pankaj Karande, Troy, NY (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/740,147

(22) PCT Filed: Jun. 30, 2016

(86) PCT No.: PCT/US2016/040497
§ 371 (c)(1),
(2) Date: Dec. 27, 2017

(87) PCT Pub. No.: WO2017/004421
PCT Pub. Date: Jan. 5, 2017

(65) Prior Publication Data
US 2018/0185350 A1 Jul. 5, 2018

Related U.S. Application Data

(60) Provisional application No. 62/186,931, filed on Jun. 30, 2015.

(51) Int. Cl.
| | |
|---|---|
| A61K 31/4745 | (2006.01) |
| A61K 38/21 | (2006.01) |
| A61K 39/395 | (2006.01) |
| A61K 41/00 | (2020.01) |
| A61K 47/12 | (2006.01) |
| A61K 47/14 | (2017.01) |
| A61K 47/20 | (2006.01) |
| A61K 9/00 | (2006.01) |
| A61P 17/12 | (2006.01) |
| A61P 35/04 | (2006.01) |
| A61K 45/06 | (2006.01) |
| A61K 39/00 | (2006.01) |
| A61K 31/444 | (2006.01) |

(52) U.S. Cl.
CPC ........ *A61K 31/4745* (2013.01); *A61K 9/0014* (2013.01); *A61K 9/0019* (2013.01); *A61K 31/444* (2013.01); *A61K 38/217* (2013.01); *A61K 39/00* (2013.01); *A61K 39/39558* (2013.01); *A61K 41/0057* (2013.01); *A61K 45/06* (2013.01); *A61K 47/12* (2013.01); *A61K 47/14* (2013.01); *A61K 47/20* (2013.01); *A61P 17/12* (2018.01); *A61P 35/04* (2018.01); *A61K 2300/00* (2013.01)

(58) Field of Classification Search
CPC .............. A61K 31/4745; A61K 9/0014; A61K 9/0019; A61K 39/39558; A61K 41/0057; A61P 35/04
See application file for complete search history.

(56) References Cited

U.S. PATENT DOCUMENTS

| | | |
|---|---|---|
| 2003/0026794 A1 | 2/2003 | Fein |
| 2004/0265351 A1* | 12/2004 | Miller .................... A61K 31/44 424/423 |
| 2005/0214328 A1 | 9/2005 | Zeldis et al. |
| 2008/0107719 A1* | 5/2008 | Likitlersuang ....... A61K 9/0009 424/449 |
| 2009/0017075 A1 | 1/2009 | Van Nest et al. |
| 2010/0056557 A1 | 3/2010 | Benninghoff et al. |
| 2010/0180902 A1 | 7/2010 | Miller et al. |
| 2011/0021524 A1 | 1/2011 | Adrian et al. |
| 2011/0136751 A1 | 6/2011 | Estrela et al. |
| 2012/0237551 A1 | 9/2012 | Statham et al. |
| 2013/0230578 A1 | 9/2013 | Wightman |
| 2013/0237561 A1 | 9/2013 | Leoni et al. |
| 2014/0205669 A1 | 7/2014 | Barth et al. |
| 2015/0110784 A1 | 4/2015 | Tomai et al. |
| 2015/0165025 A1 | 6/2015 | Korman et al. |

FOREIGN PATENT DOCUMENTS

| | | | |
|---|---|---|---|
| EP | 2 394 650 A1 | | 12/2011 |
| WO | 2007079203 A2 | | 7/2007 |
| WO | WO 2013/043647 | * | 3/2013 |
| WO | 2014/107663 A2 | | 7/2014 |
| WO | WO2014/107663 | * | 7/2014 |
| WO | 2015017378 A2 | | 2/2015 |

OTHER PUBLICATIONS

Chang et al. Vaccine 27, 5791-5799 (2009) (Year: 2009).*
NCI Dictionary of Cancer Terms at www.cancer.gov/publications /dictionaries/cancer-terms?expand=l (Year: 2018).*
Weide et al. in Cancer 116:4139-4146 (2010) (Year: 2010).*
Baldea et al. ion Journal of Physiology and Pharmacology 63(2): 109-118 (2012) (Abstract) (Year: 2012).*
National Cancer Institute—Photodynamic Therapy for Cancer (2011) (https://www.cancer.gov/about-cancer/treatment/types/surgery/photodynamic-fact-sheet) (Year: 2018).*
Li et al. in Clinical Pharmacology 5(suppl 1):47-53 (2013) (Year: 2013).*
Brouckaert et al. in International Journal of Cancer: 38, 763-769 (1986) (Year: 1986).*

(Continued)

*Primary Examiner* — Dennis Heyer
(74) *Attorney, Agent, or Firm* — Kathleen D. Rigaut; Howson & Howson LLP

(57) ABSTRACT

Compositions and methods for treatment of viral skin disease, precancerous and cancerous skin disease, and other neoplasms are disclosed.

19 Claims, 18 Drawing Sheets

(56) References Cited

OTHER PUBLICATIONS

Sabado et al. in Journal of ImmunoTherapy of Cancer 2013 1 (Suppl 1) p. 272 (Year: 2013).*
Amiji et al. in Pharmaceutical Development and Technology, 7(2), 195-202 (2002) (Year: 2002).*
Lugade et al. in Journal of Immunology 174: 7516-7523 (2005) (Year: 2005).*
Davis et al. in Clinical Cancer Research 17(12): 3984-3992 (2011) (Year: 2011).*
Dovedi et al. in Blood. 2013;121(2):251-259 (Year: 2013).*
Fox, C.B. in Molecules 2009, 14, 3286-3312. (Year: 2009).*
Adams, Sylvia et al., "Topical TLR7 agonist iniquimod can induce immune-mediated rejection of skin metastases in patients with breast cancer", Clin. Cancer Res., 18(24): 6748-6757 (2012).
Qiang, Yong-Gang et al., "Combination of photodynamic therapy and immunomodulation—current status and future trends", Med. Res. Rev., 28(4): 632-644 (2008).
International Search Report and Written Opinion, dated Sep. 13, 2016, issued in corresponding International Application No. PCT/US16/40497.
Sabado, Rachel Lubong et al., "Resiquimod as an Immunologic Adjuvant for NY-ESO-1 Protein Vaccination in Patients with High Risk Melanoma", Cancer Immunol. Res., 3(3): 278-287 (2015).
Singh, Manisha et al., "Effective Innate and Adaptive Antimelanoma Immunity through Localized TLR7/8 Activation", The Journal of Immunology, 193: 4722-4731 (2014).

\* cited by examiner

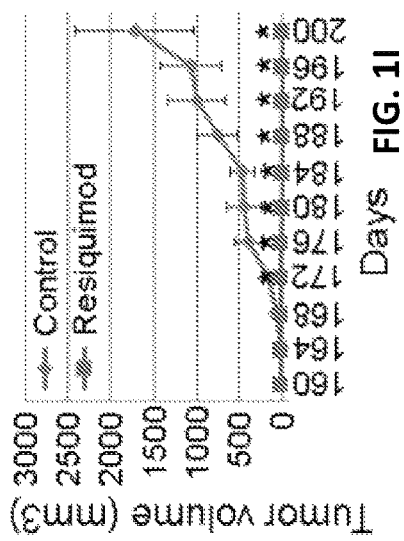
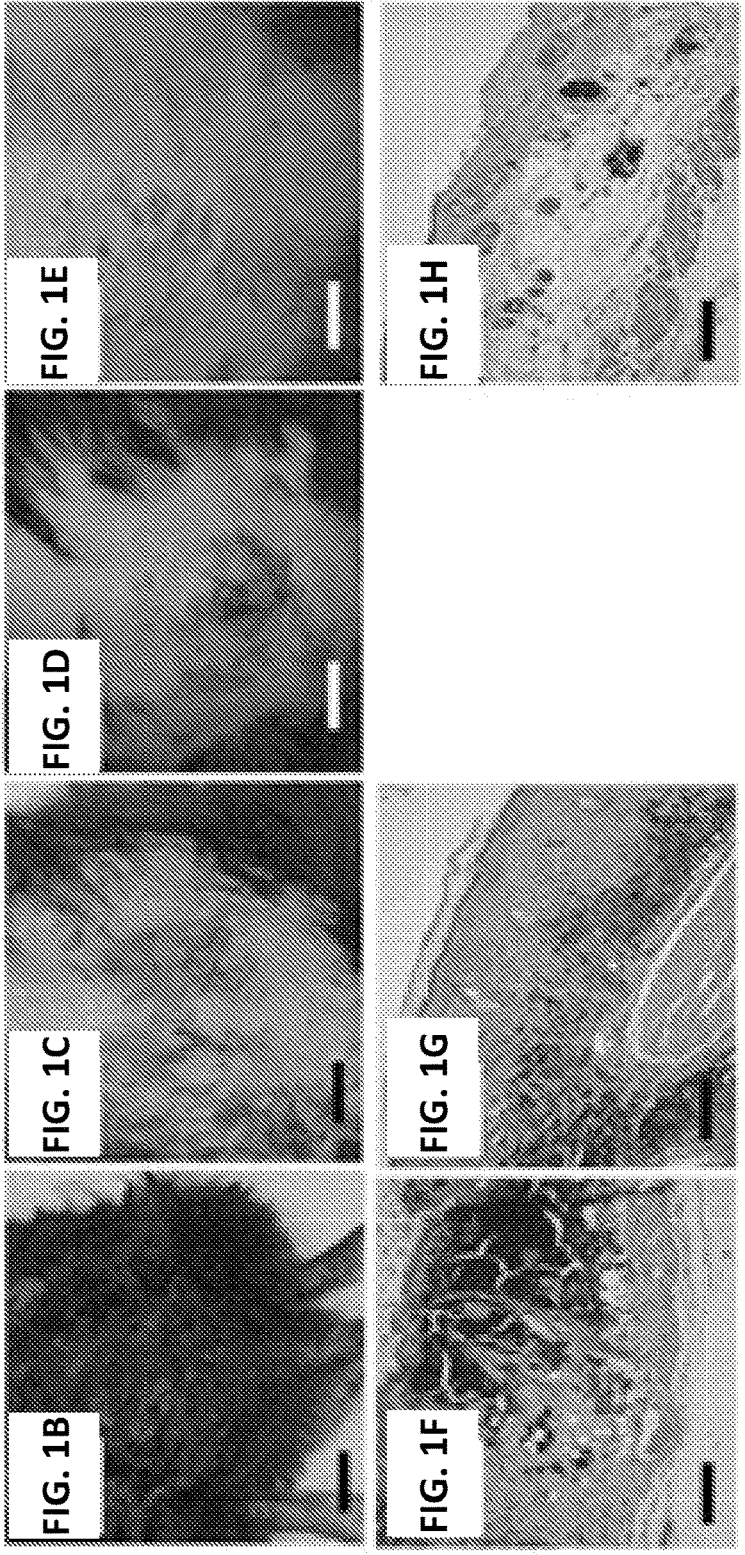

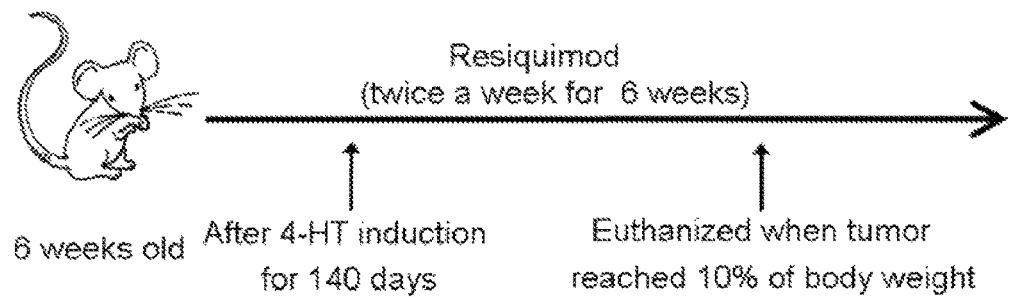
FIG. 2A
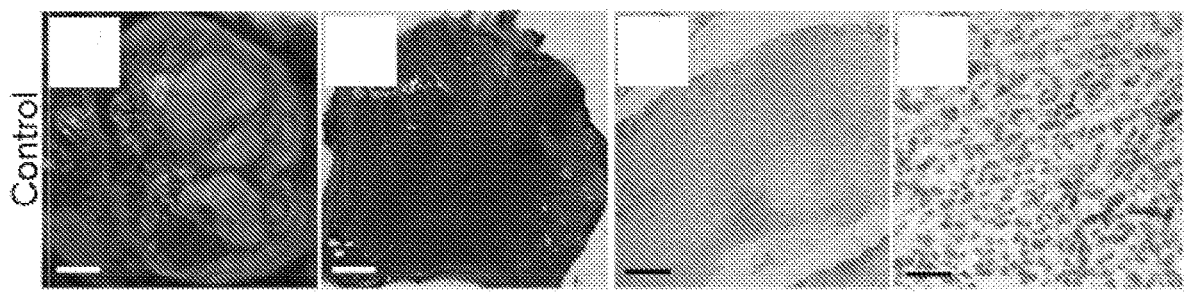
FIG. 2B     Fig. 2C     Fig. 2D     FIG. 2E
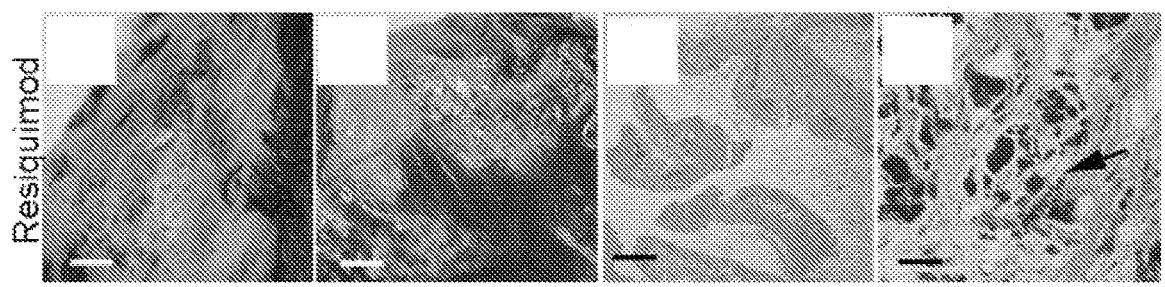
FIG. 2F     Fig. 2G     Fig. 2H     FIG. 2I
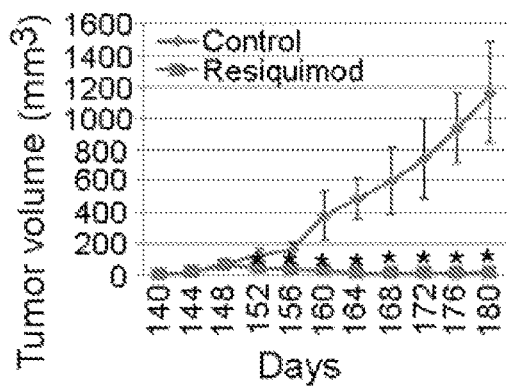
FIG. 2J
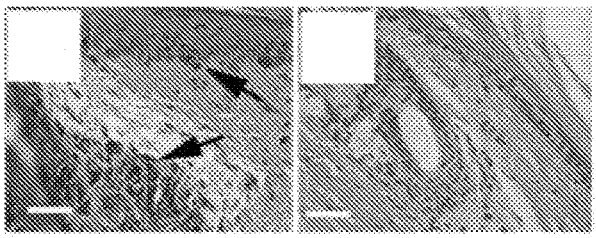
FIG. 2K     FIG. 2L

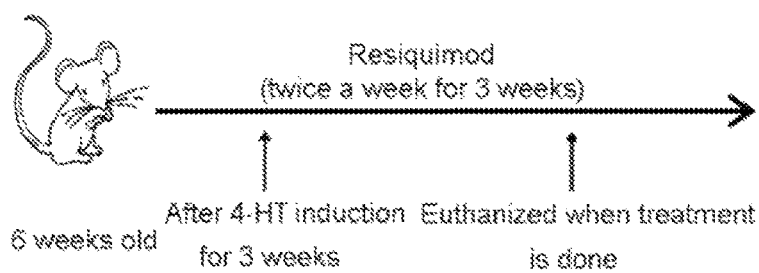
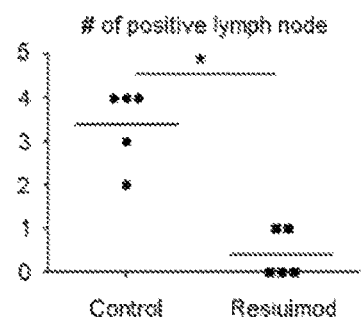
FIG. 4A  FIG. 4B
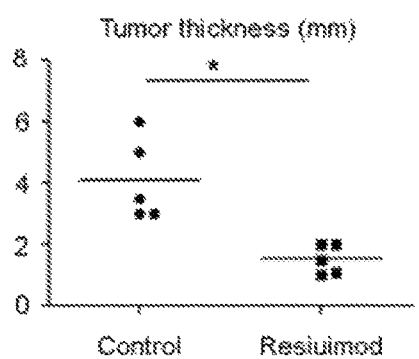
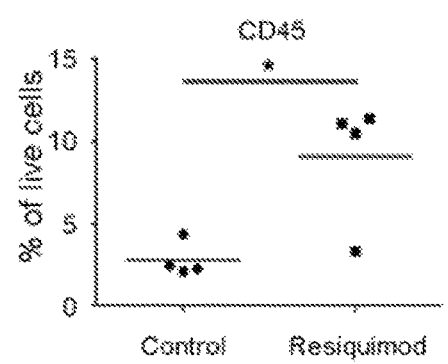
FIG. 4C  FIG. 4D
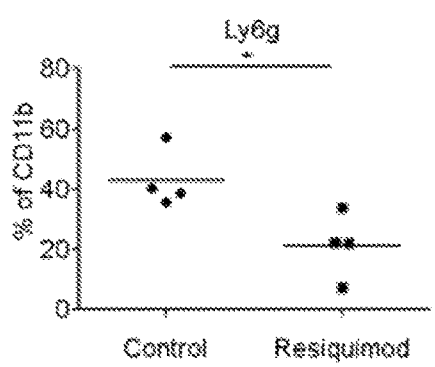
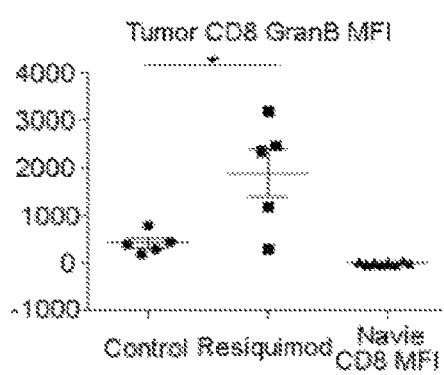
FIG. 4E  FIG. 4F
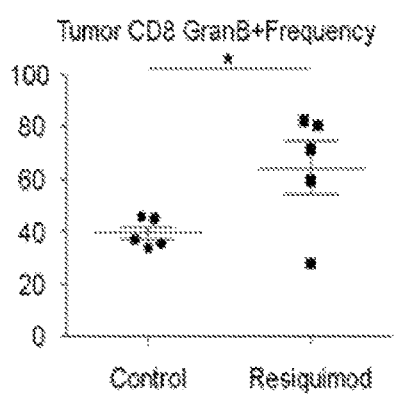
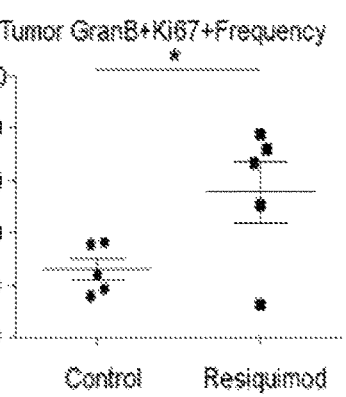
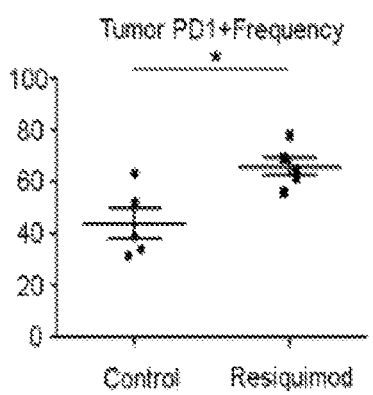
FIG. 4G  Fig. 4H  FIG. 4I

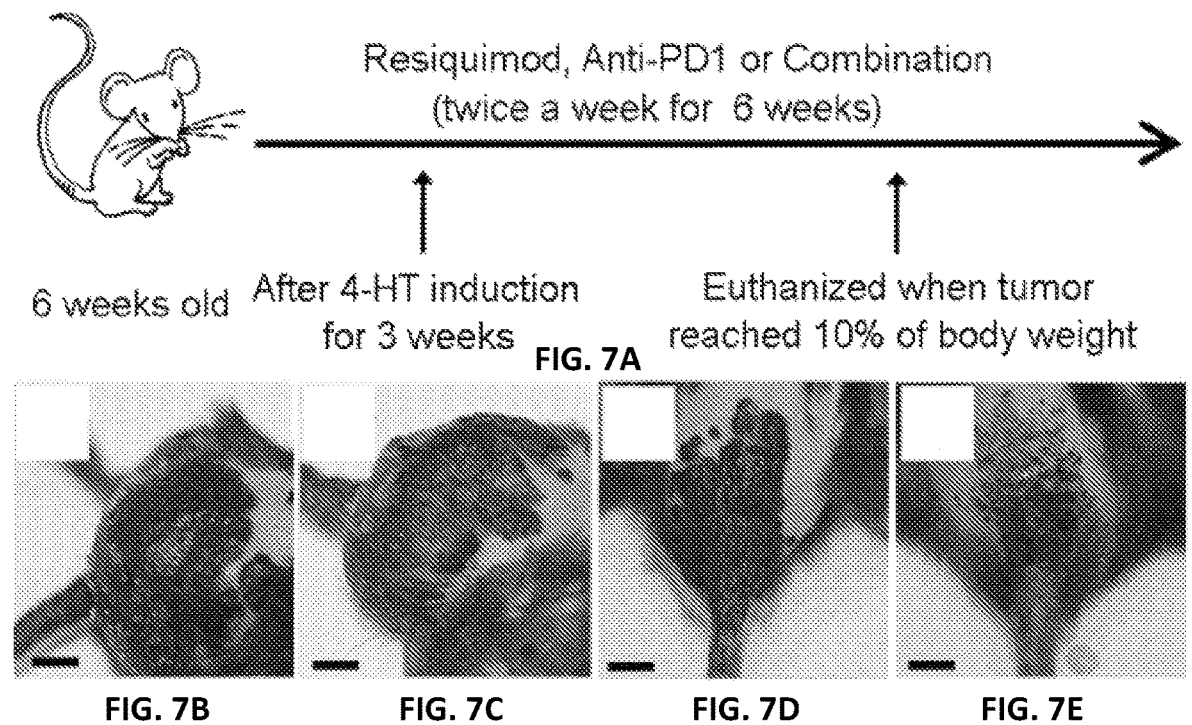
FIG. 7A
FIG. 7B
FIG. 7C
FIG. 7D
FIG. 7E
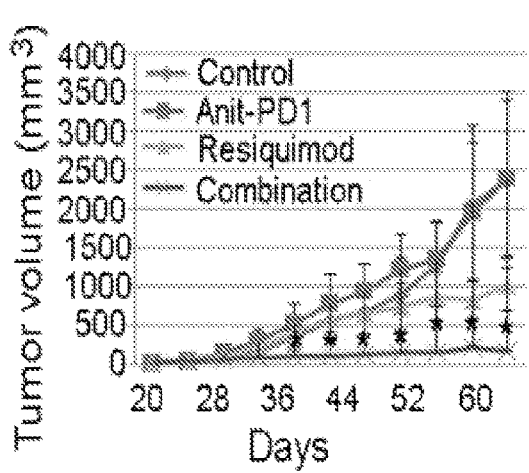
FIG. 7F
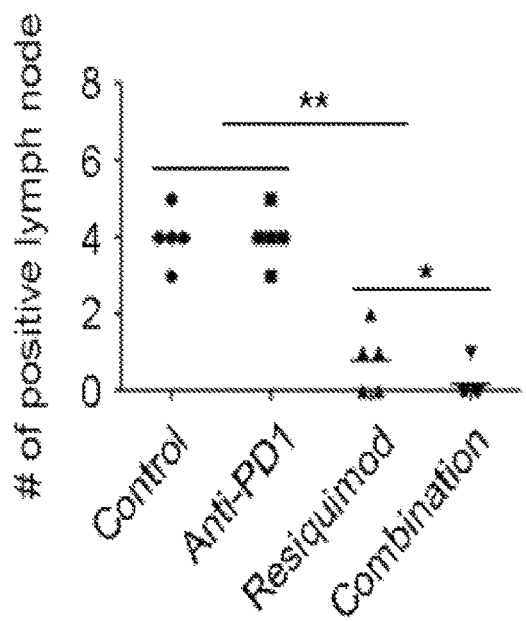
FIG. 7G

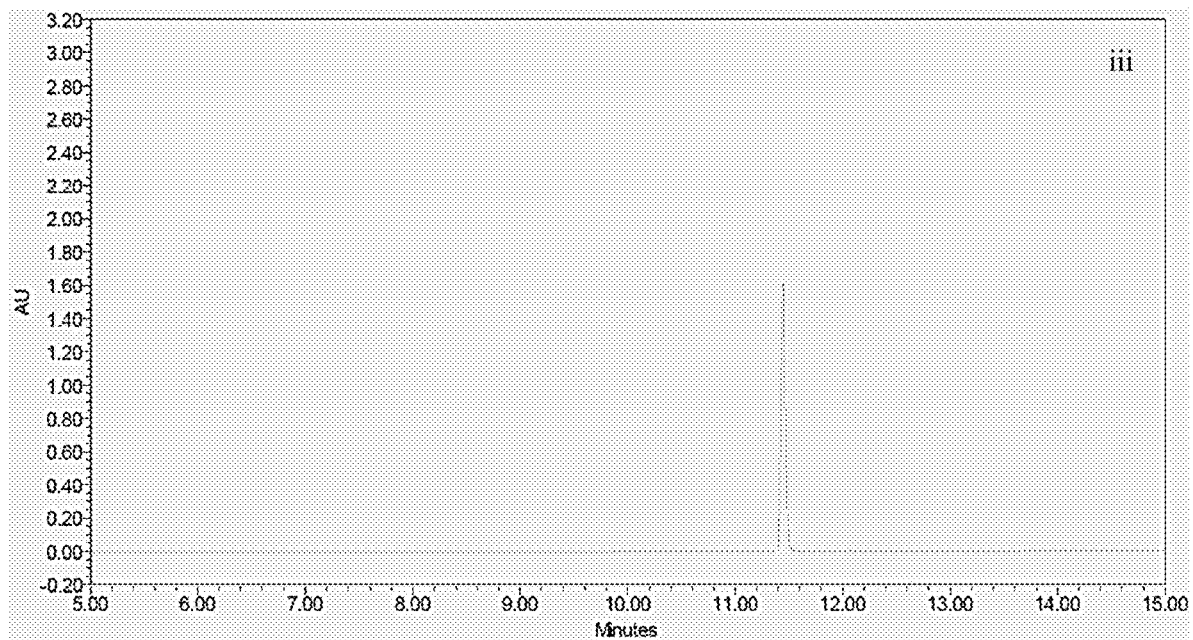
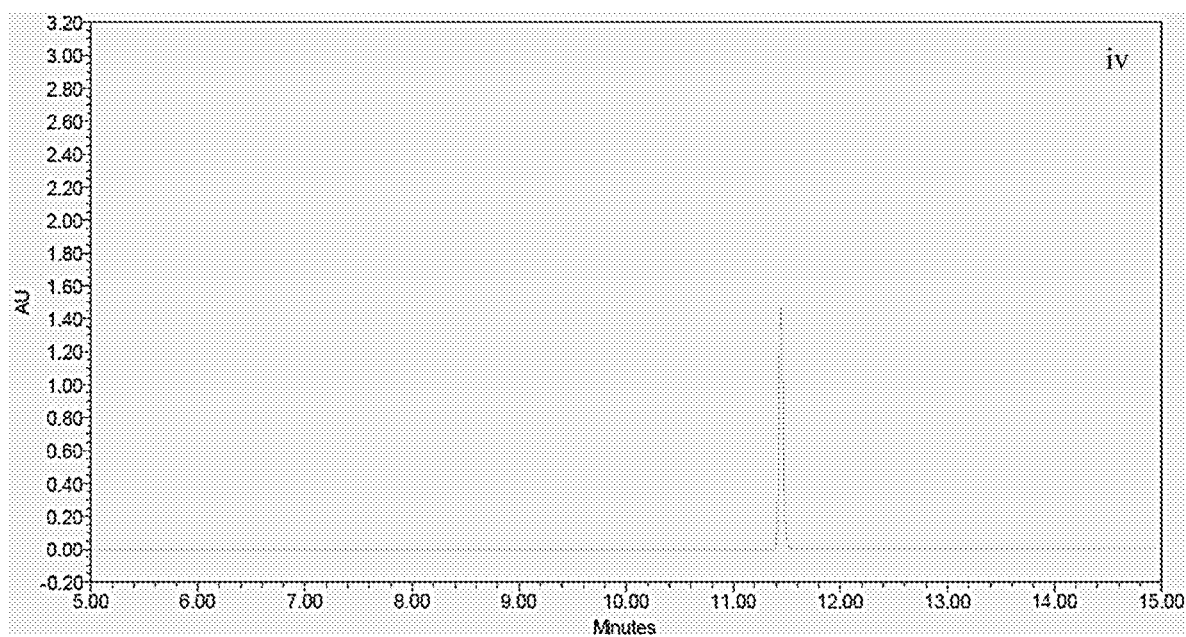
FIG. 8B

RESIQUIMOD TOPICAL AND INJECTABLE COMPOSITIONS FOR THE TREATMENT OF NEOPLASTIC SKIN CONDITIONS

CROSS-REFERENCE TO RELATED APPLICATIONS

This application is a § 371 of the International Application No. PCT/US2016/040497, filed Jun. 30, 2016, which claims priority to U.S. Provisional application No. 62/186,931, filed Jun. 30, 2015. The entire disclosure of each of the aforesaid applications being incorporated herein by reference in the present application as though set forth in full.

GOVERNMENT SUPPORT INTEREST

This invention was made with government support under grant number AR054593 awarded by the National Institutes of Health. The government has certain rights in the invention.

FIELD OF THE INVENTION

This invention relates to the fields of dermatology and oncology. More specifically, the invention provides resiquimod containing compositions for treatment of non-cancerous skin disorders, pre-cancerous skin disorders, primary and metastatic neoplasms of the skin and other tissues.

BACKGROUND OF THE INVENTION

Several publications and patent documents are cited throughout the specification in order to describe the state of the art to which this invention pertains. Each of these citations is incorporated herein by reference as though set forth in full.

Skin cancer is the most commonly diagnosed form of cancer of which, the non-melanoma skin cancers, basal cell carcinoma and squamous cell carcinoma, are the most common types. Non-melanoma skin cancers are most often treated with surgical excision. Non-surgical treatments are employed but only in a minority of patients due to limited efficacy or cost. Melanoma results in the greatest number of skin cancer-related deaths worldwide. Melanoma is the $5^{th}$ most common cancer in men and the $6^{th}$ most common cancer in women. It is the most common form of cancer for young adults 25-29 years old, particularly in young women. In situ melanoma is the very earliest stage of melanoma. There are cancer cells in the top layer of skin (the epidermis) but they are all contained in the epidermis where they start to develop. By curing melanoma in situ, invasive melanoma can be prevented. Many therapies have been investigated for the treatment of localized cutaneous melanoma either as an adjuvant or in place of surgical therapy.

Pre-cancerous skin lesions are more common than malignant lesions. These precancerous lesions are indicative of changes in skin that are not yet cancer but could become cancer over time. Pre-cancerous pigmented lesions, including atypical melanocytic lesions, atypical melanocytic hyperplasia, and atypical intraepidermal melanocytic exhibit high proliferation levels. Some of these lesions are thought to have the potential for developing into melanoma. Classification of lesions is typically based on visual or pathologic inspection of the lesion. In order to prevent or inhibit progression to malignancy, new treatment protocols for such pre-cancerous lesions are urgently needed.

Similar to skin, bladder also has a surface lining that has cancerous transformation potential. Early bladder cancer is also called superficial bladder cancer or nonmuscle invasive bladder cancer. This means that the cancer cells are only in the inner lining of the bladder. In CIS (carcinoma in situ) the cancer cells are still only in the bladder lining of the bladder. They are in flat sheets that look a bit like moss. CIS can occur in patches throughout the bladder lining and the cells are very abnormal. This cancer is associated with a high risk of spreading into the deeper layers of the bladder. Early stage bladder cancer may be treated with BCG vaccine administration into the bladder. By curing CIS, invasive cancer can be prevented. However, current nonsurgical therapy for early bladder cancer is very limited.

When cancerous lesions progress, they may become metastatic and chemotherapy, radiation therapy and immunotherapy may be used in addition to surgery. Resiquimod, a member of the imidazoquinoline family related in structure to imiquimod, is an immune response modifier which acts as a Toll-like receptor 7 and 8 agonist. However, it is distinctively different from Imiquimod since Imiquimod signals through the toll-like receptor 7 (TLR7) only. Imiquimod is FDA approved for the treatment of a number of skin diseases. Compared with imiquimod, resiquimod is a more potent inducer of IFN-α, TNF-α, IL-1, IL-6, IL-8, and IL-12. Although resiquimod has been shown to be 10-100× more potent than imiquimod in T cell activation, it has not yet been approved for clinical use by the FDA. Resiquimod has been shown to promote cross-presentation of exogenous antigens, resulting in the efficient induction of antigen-specific $CD8^+$ T-cell responses in an animal model. Results from animal studies have confirmed the ability of resiquimod to activate dendritic cells, including the capacity to induce local activation of immune cells, stimulate the production of proinflammatory cytokines, and enhance antigen-presentation by dendritic cells leading to activation of effective cellular responses. Systemic delivery of resiquimod, with radiation, primes durable antitumor immune responses in a lymphoma model (Dovedi S J 2013, Blood 121(2):251-9.). Resiquimod has been used in clinical trials to treat actinic keratosis, cutaneous T cell lymphoma and herpes simplex virus with mixed results. Other prior art uses of resiquimod include administration as a vaccine adjuvant agent to treat various diseases, including metastatic melanoma with inconsistent results. Resiquimod has been used as a vaccine adjuvant for NY-ESO-1 protein vaccine in treatment of melanoma (Sabado R L Cancer Immunol Res. 2015).

A major advance in clinical immunotherapy has been the blockade of inhibitory immune receptors and their ligands, collectively termed immune checkpoints. Specifically, blockade of CTLA4 and PD1 (or PDL1) has demonstrated clinical efficacy in a number of different advanced malignancies. However, the response rate is still relatively low in clinical trials and there is an unmet clinical need to combine immune checkpoint blocks with other reagents.

SUMMARY OF THE INVENTION

In accordance with the present invention, compositions and formulations comprising an effective amount of resiquimod and methods of use thereof for the treatment of non-cancerous, pre-cancerous, and cancerous lesions are disclosed. In a preferred embodiment of the invention, a composition comprising between 0.01%-1% resiquimod for the treatment of various diseases is provided. The inventive formulations are formulated for local (topical, intracystic and intratumoral) administration, enhance permeation and delivery of resiquimod, and facilitate beneficial local immune reactions while limiting adverse reactions such as erythema, inflammation or systemic cytokine release. Topical, intracystic and intratumoral formulations are different as they are specifically formulated to maximally enhance resiquimod's therapeutic effects while also reducing unwanted side effects. In a particularly preferred embodiment, the precancerous lesion is selected from actinic keratosis, an atypical junctional melanocytic lesions, atypical melanocytic hyperplasia, atypical intraepidermal melanocytic hyperplasia, atypical intraepidermal melanocytic proliferation. In alternative embodiments, the cancerous lesion is basal cell carcinoma, squamous cell carcinoma, lentigo maligna, melanoma in situ and melanoma. The neoplasm may also be selected from Bowen's disease, squamous cell carcinoma in situ, arsenical keratosis, radiation keratosis, PUVA keratosis, bowenoid papulosis, sebaceous carcinoma, porocarcinoma, extramammary Paget's disease, Merkel cell carcinoma, Kaposi's sarcoma and cutaneous T cell lymphoma. The composition also has efficacy for the treatment of abnormal epidermal keratinocyte proliferation, and seborrheic keratosis. The composition also has efficacy for the treatment of viral skin infections, such as, HPV infections including vulvar intraepithelial neoplasia, vaginal intraepithelial neoplasia, common warts that are difficult to treat, molluscum contagiosum and HSV infection. In alternative embodiments, the cancerous lesion is bladder carcinoma in situ and early bladder cancer (superficial bladder cancer or nonmuscle invasive bladder cancer).

In another aspect, the resiquimod is administered in combination with interferon gamma for the treatment of basal cell carcinoma, squamous cell carcinoma, bladder superficial carcinoma, lentigo maligna, melanoma in situ, primary invasive melanoma and cutaneous T cell lymphoma. Use of resiquimod in combination with radiation therapy for the treatment of basal cell carcinoma, squamous cell carcinoma, bladder superficial carcinoma, lentigo maligna, melanoma in situ, primary invasive melanoma and cutaneous cell lymphoma also forms an aspect of the invention. Use of resiquimod in combination with photodynamic therapy for the treatment of basal cell carcinoma, squamous cell carcinoma, bladder superficial carcinoma, lentigo maligna, melanoma in situ, primary invasive melanoma and cutaneous T cell lymphoma is also disclosed.

In a particularly preferred embodiment of the invention, a method for the treatment of non-cancerous, pre-cancerous, and cancerous neoplasms of the skin and bladder, comprising topical or intracystic administration of the composition(s) described above is provided wherein the composition is effective to reduce or eliminate said lesion.

When the method is for the treatment of deep cancer or metastatic tumors including melanoma, intratumoral injection of resiquimod or intratumoral resiquimod with systemic administration of one or more immune modulators, including, for example, anti-PD1, anti-PDL1, Anti-CTLA-4 antibodies, CD137 (Urelumab), CD40, CD134 (Anti-OX40) agonist and other immune-modulating small molecules that can inhibit MDSCs (such as PLX3397) is preferred. The intratumoral formulations and methods of use thereof can be used to advantage to treat a wide variety of pathological conditions, including without limitation, metastatic epithelial cancer, squamous cell carcinoma, basal cell carcinoma, lung, bladder, prostate, brain, breast, pancreas, ovary, liver, stomach, other epithelial malignant tumor cells and mesenchymal malignant tumor cells such as soft tissue sarcomas as well as hematopoietic malignancy such as lymphoma and advanced cutaneous T cell lymphoma.

In a particularly preferred embodiment of the invention, a method for the treatment of deep or metastatic tumor, comprising intratumoral administration of the composition (s) alone or in combination of systemic administration of anti-PD1, or anti-PDL1, or Anti-CTLA-4 antibodies or CD137 (Urelumab), CD40, CD134 (Anti-OX40) agonist and other immune-modulating small molecules that can inhibit MDSCs (such as PLX3397) described above is provided wherein the composition is effective to reduce or eliminate said lesion.

BRIEF DESCRIPTION OF THE DRAWINGS

FIGS. 1A-1I. Resiquimod inhibits tumor growth in Tyr:: creER, BRAF$^{ca}$ mice. FIG. 1A) Treatment scheme. FIG. 1B) Large pigmented lesion in a mouse treated with vehicle (n=5). FIG. 1C) Residual dermal pigmentation in a mouse treated with resiquimod (n=8). FIG. 1D) Pigmented lesion in a mouse before treatment. FIG. 1E) The same lesion 1 month after resiquimod treatment. FIG. 1F) Histology of tumor treated with vehicle. There are many tumor cells in the dermis. FIG. 1G) Histology of tumor treated with resiquimod. Viable tumor cells are not seen and many macrophages with pigmentation are seen in the dermis. FIG. 1H) Histology of the lesion one month after resiquimod treatment. Viable tumor cells are not seen and only macrophages with pigmentation are seen in the dermis. FIG. 1I) Tumor growth curve of mice treated with vehicle or resiquimod. *indicate $p<0.05$. Bars in b-e indicate 6 mm. Bars in f-h indicate 200 μm.

FIGS. 2A-2L. Resiquimod inhibits melanoma growth in Tyr::creER, BRAFca, Phd2lox/lox mice. FIG. 2A) Treatment scheme. FIG. 2B) Large tumor in a mouse treated with vehicle (n=10). FIG. 2C) Underside of skin filled with tumor. FIGS. 2D and 2E) Histology of melanoma in a control mouse. The dermis is filled with tumor cells. FIG. 2F) Resiquimod treated mouse with near complete response (n=10). FIG. 2G) Underside of skin cleared of tumor. FIG. 2H) Histology of skin in a treated mouse, normal appearing. FIG. 2I) Macrophages with pigment are present in the dermis in a treated mouse. Arrow points to macrophages. FIG. 2J)Tumor growth curve. FIG. 2K) In situ melanoma in control mice. Arrows point to the tumor cells in the epidermis and hair follicle. I) Normal appearing epidermis in treated mice. *indicates $p<0.05$. Bars in b, c, f and g indicate 6 mm. Bars in d, e, h and I, indicate 200 μm. Bars in k and l indicate 10 μm.

FIG. 3A) Treatment scheme. FIG. 3B) Representative image of a mouse with control treatment (n=15). FIG. 3C) Representative image of a mouse with resiquimod treatment (n=15). FIG. 3D) Histology of melanoma in a control mouse. Arrow points to skeletal muscle. FIG. 3E) Histology of melanoma in a treated mouse. Arrow points to skeletal muscle. FIG. 3F) Effect of resiquimod on tumor volume. FIG. 3G) Effect of resiquimod on mouse survival. FIG. 3H) In situ melanoma in control mice. Arrows point to the tumor cells in the epidermis. FIG. 3I) Normal appearing epidermis in treated mice. *indicates $p<0.05$. Bars indicate 6 mm in FIG. 3B and FIG. 3C, 400 μm in FIG. 3D and FIG. 3E and 50 μm in FIG. 3H and FIG. 3I.

FIGS. 4A-4I. Reprogramming of tumor immune microenvironment after resiquimod treatment. FIG. 4A) Treatment scheme. FIG. 4B) Effect of resiquimod on positive lymph nodes (n=5). FIG. 4C) Effect of resiquimod on tumor thickness. FIG. 4D) Effect of resiquimod on intratumoral $CD45^+$ cells. FIG. 4E) Effect of resiquimod on intratumoral M-MDSCs. FIG. 4F) Effect of resiquimod on intratumoral GramB MFI in $CD8^+$ cells. FIG. 4G) Effect of resiquimod on intratumoral $GramB^+CD8^+$ T cells. FIG. 4H) Effect of resiquimod on intratumoral $GramB^+CD8^+ki-67^+$ cells. FIG. 4I) Effect of resiquimod on intratumoral PD1 $^+CD8^-$ cells. All measurement was compared to the control. *indicates $p<0.05$.

FIG. 5A) Treatment scheme. FIG. 5B) Effect of resiquimod on melanoma growth (n=10). FIG. 5C) Effect of resiquimod on mouse survival. FIG. 5D) Histology of melanoma from a control (left) and resiquimod (right) treated mouse. There are more inflammatory cells in the treated mice. Arrow points to the inflammatory cells. FIG. 5E) Fold changes in cytokine and chemokine mRNA expression in the tumor tissues from treated mice compared to control mice. *indicates $p<0.05$. Bars in d indicate 25 μm.

FIG. 6A) Effect of resiquimod on Rag-1-deficient mice. The survival curves showed that the effect of resiquimod was abolished in these mice. FIG. 6B) Effect of resiquimod on CD8-depleted mice. The survival curves showed that the effect of resiquimod was abolished in these mice. FIG. 6C) Effect resiquimod on cytokine release by T cells after stimulation.

FIGS. 7A-7G. Combination of resiquimod and anti-PD1 therapy dramatically reduced melanoma growth. FIG. 7A) Treatment scheme. FIGS. 7B-7E) Representative images of mice treated with control vehicle (FIG. 7B), anti-PD1 (FIG. 7C), resiquimod (FIG. 7D) and resiquimod+anti-PD1 (FIG. 7E). FIG. 7F) Effect of therapies on melanoma growth (n=5 each group). FIG. 7G) Effect of therapies on lymph node metastasis. *indicates $p<0.05$. **indicates $p<0.01$. Bars indicate 6 mm.

FIGS. 8A-8D. Stability and solubility of resiquimod in a topical formulation consisting of a combination on ethanol and phosphate buffered saline (PBS). FIG. 8A-8C) HPLC chromatograms of resiquimod formulations at different compositions in a representative 50:50 ethanol:pbs topical formulation aged for 2 weeks. The chromatograms exhibit that resiquimod is stable and soluble in the base formulation without degradation or formation of by-products as noted by the presence of a single peak and consistent retention times on a C18 column at various concentrations in the base formulation. All data are collected under the following gradient conditions: 0-5 mins:100% Water; 5-15 mins: 0 to 100% Acetonitrile gradient; 15-20 mins: 100% Acetonitrile; 20-25 mins 100% to 0% Acetonitrile gradient; 25-30 mins: 100% Water in a 10 μL injection containing (i) 16 nM; (ii) 12.7 nM; (iii) 9.5 nM; (iv) 6.4 nM; (v) 1.6 nM and (vi) 0.16 nM resiquimod. FIG. 8D) A calibration curve showing area under the curve of resiquimod as a function of the number of moles of resiquimod present in the formulation. The strong statistical correlation further indicates that resiquimod is stable and soluble in a pbs:ethanol formulation.

FIG. 9A) Human skin permeability of resiquimod from a formulation containing 50:50 PBS:ethanol (denoted as control), a formulation containing 10% (vol/vol) oleic acid as a chemical enhancer (denoted as Formulation 1) and a formulation containing sodium lauryl sulfate (5%) and oleic acid (2%) as chemical enhancers (denoted as Formulation 2) at 6 hrs. These data demonstrate that chemical permeation enhancers can significantly accelerate the topical delivery of resiquimod across human skin as early as 6 hrs thereby reducing the total topical dosage and/or reduction in lag time for delivery of resiquimod to target for biological activity. FIG. 9B) Amount of resiquimod delivered across the skin from three different formulations in 6 hrs. FIG. 9C) Permeation of resiquimod across human skin in three different formulations at 18 hrs is shown. These data show enhanced permeation and enhanced delivery of resiquimod across human skin in presence of permeation enhancers compared to base formulation. FIG. 9D) Amount of resiquimod delivered across the skin from three different formulations in 18 hrs.

FIG. 10. Adjuvancy potential of topical formulations. The secretion of cytokine interleukin 1 alpha (IL-1α) from skin tissue measured from 10 unique formulations that are also topical permeation enhancers of varying efficacies. IL-1α is a representative cytokine and marker of tissue inflammation implicated in innate immune response.

DETAILED DESCRIPTION OF THE INVENTION

Skin cancer is usually superficially located. Melanoma in situ is still confined to the epidermis and typically grows slowly. Such lesions may take years to progress to invasive melanoma. Invasive melanoma usually has an epidermal component but is no longer confined to the epidermis as melanoma cells invade the dermis. Metastatic cancer is usually deeply located. Because the effectiveness of resiquimod requires the presence of functional dendritic and T cells, it is currently impractical to test the function of tumor killing effect of resiquimod in vitro. In accordance with the present invention, we provide data demonstrating that resiquimod functions in multiple in vivo pigmented lesion transgenic mouse models and in a syngeneic melanoma mouse model which have an intact immune system. Our data showed that resiquimod was effective in inhibiting or killing melanocytic tumor cells in nevus, atypical intraepidermal melanocytic proliferation and melanoma. In addition, the mice treated with resiquimod also had significantly reduced metastatic melanoma in the lymph nodes, indicating that resiquimod can inhibit melanoma cell metastasis. Additionally we showed that resiquimod in combination with systemic anti-PD1 therapy significantly enhanced the anti-PD-1 therapeutic effects in melanoma models. Importantly, our data indicate that resiquimod induced an influx of CD45 positive leukocytes in the tumor and the effect of resiquimod is mediated through both activation of CD8+ T cells and inhibition of myeloid-derived suppressor cells. The implication of our discovery is broad. Since the effect of resiquimod on tumors is mediated through activation of CD8 T cells and inhibition of myeloid-derived suppressor cells, the effect of resiquimod is not limited to melanocytic tumors. It is also effective in treating other epithelial cancers and cutaneous T-cell lymphoma.

Because metastatic cancer including melanoma is often in the subcutis, or at other internal sites, topical application of resiquimod is unlikely to reach these sites. To further improve the treatment efficacy of resiquimod in late stage cancer/melanoma patients, we developed an injectable form of resiquimod. We found that even high doses of resiquimod injection did not cause significant toxicity in mice, thus indicating that injectable resiquimod is safe. Accordingly, the invention provides use of a novel, injectable formulation of resiquimod alone or in combination, with anti-PD1, or anti-PDL1, or Anti-CTLA-4 antibodies or CD137 (Urelumab), CD40, CD134 (Anti-OX40) agonist and other immune-modulating small molecules that can inhibit MDSCs (such as PLX3397). This formulation, alone or in combination, and methods of use thereof can be used advantageously to treat a wide variety of pathological conditions, including without limitation, metastatic epithelial cancer, squamous cell carcinoma, basal cell carcinoma, lung, bladder, prostate, brain, breast, pancreas, liver, stomach, other epithelial malignant tumor cells and mesenchymal malignant tumor cells such as soft tissue sarcomas as well as hematopoietic malignancy such as B cell lymphoma, leukemia and advanced cutaneous T cell lymphoma.

Figure 3A:
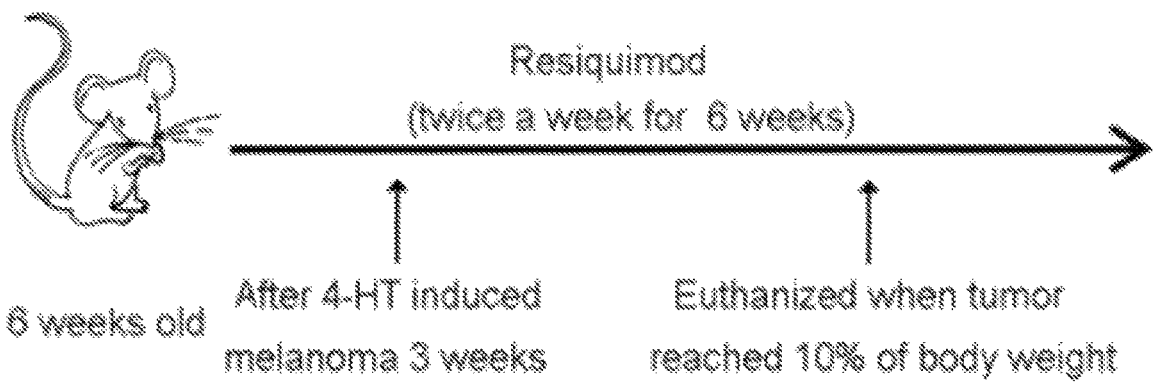
FIGS. 3A-3I. Resiquimod inhibits melanoma growth in Tyr::creER, BRAFca, Ptenlox/lox mice.

Injectable formulations provide several advantages for achieving enhanced penetration/permeation and/or immune adjuvancy via the use of chemical moieties. US patent 2004/0265351 A1 (incorporated herein by reference) teaches methods for localizing and retaining drugs like resiquimod within a tissue environment. This is achieved by use of purified oils (soybean oil, safflower oil, triolein, and castor oil, fractionated coconut oil, miglyol810, 812, Neobee MS, Captex 300) and FDA approved dermal fillers (hydroxylapatite, hyaluronic acid, Poly-L-Lactic Acid, collagen, hydrogel) as components of injectable formulation. The present invention includes novel applications of chemical moieties, including for example, vehicles, gels and carriers for retarding the diffusion of resiquimod from the site of injection using a single component or a plurality of components towards this end. In one approach, resiquimod is formulated in a solvent that ensures stability and solubility for topical and injectable administration (See FIG. 8). Notably, inclusion of chemical enhancers facilitates the enhanced diffusion of the active ingredient, resiquimod, locally across the tumor matrix (largely composed of cells and extracellular matrix components) which is apparent from the data presented in FIG. 9. Additionally, chemical enhancers have the ability to cause local inflammation that is conducive to the initiation and acceleration of an immune response by facilitating the secretion of cytokines that are agents of inflammation and mediators of the innate immune response. It is well-known that the innate immune response synergizes with the adaptive immune response and is beneficial in the overall activity against tumors and malignant cells. This follows from the data presented in FIG. 10 on the ability of chemicals to initiate the secretion of interleukin 1 alpha (IL-1α) in skin. IL-1α is a known marker of non-specific inflammation in tissues and provides a surrogate measure of adjuvancy activity. Moieties capable of inducing localized inflammation and tissue penetration enhancement include, but are not limited to, members of a broad class of chemicals including sulfoxides, alcohols, polyols, alkanes, fatty acids, esters, amines and amides, terpenes, surface-active agents, cyclodextrins, $C_2$ or $C_3$ alcohols and higher, a $C_3$ or $C_4$ diol or higher, DMSO, DMF, DMA and related solvents, 1-n-dodecyl-cyclazacycloheptan-2-one, N-methyl-pyrrolidone and N-(2-hydroxyethyl) pyrrolidone, and a broader class of azones, and mixtures (binary, ternary or higher) thereof, that are otherwise pharmacologically and chemically inert and chemically stable, potent, nonsensitizing, nonphototoxic, noncomedogenic in ways other than their claimed activities. Typical concentration ranges in which such agents are employed depend on the specific agent employed but are within a range of 0.01-50% wt/vol unless constrained by their solubility in a base formulation that contains 0.5-50% vol/vol of ethanol in phosphate buffered saline.

The following definitions are provided to facilitate an understanding of the present invention. They are not intended to limit the invention in any way.

"Agonist" refers to a compound that can combine with a receptor (e.g., a TLR) to induce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR6 agonist) or a particular combination of TLRs (e.g., a TLR 7/8 agonist—an agonist of both TLR7 and TLR8).

"Ameliorate" refers to any reduction in the extent, severity, frequency, and/or likelihood of a symptom or clinical sign characteristic of a particular condition.

"Cell-mediated immune activity" refers to a biological activity considered part of a cell-mediated immune response such as, for example, an increase in the production of at least one $T_{H1}$ cytokine.

"Immune cell" refers to a cell of the immune system, i.e., a cell directly or indirectly involved in the generation or maintenance of an immune response, whether the immune response is innate, acquired, humoral, or cell-mediated.

"Sign" or "clinical sign" refers to an objective physical finding relating to a particular condition capable of being found by one other than the patient.

"Symptom" refers to any subjective evidence of disease or of a patient's condition. "Treat" or variations thereof refer to reducing, limiting progression, ameliorating, or resolving, to any extent, the symptoms or signs related to a condition.

"Penetration enhancer" and "permeation enhancement" as used herein relates to an agent and the increase in the permeability of tissue to a drug respectively, i.e., so as to increase the rate and extent at which the drug permeates through a tissue such as skin or a tumor. The enhanced permeation effected through the use of such enhancers can be observed, for example, by measuring the rate of diffusion of drug through animal or human skin or tumor tissue using a diffusion cell apparatus or in situ measurements. The diffusion cell is described by Merritt et al. Diffusion. Apparatus for Skin Penetration, J. of Controlled Release, 1 (1984) pp. 161-162.

"Adjuvancy" as used here relates to the ability to influence a nonspecific inflammation or specific immune response caused by an activator of the immune system.

As used herein, the term "anti-cancer response" to therapy relates to any response of the cancer to therapy, preferably to a change in tumor mass and/or volume after initiation of therapy. Hyperproliferative disorder response may be assessed where the size of a tumor after topical or systemic intervention is compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of therapy, e.g., after a few hours, days, weeks or preferably after a few months. A typical endpoint for response assessment is upon termination of chemotherapy or upon surgical removal of residual tumor cells and/or the tumor bed. This is typically three months after initiation of therapy.

As used herein "decreasing the size of a tumor" is defined as a reduction in the size of a tumor. Such an effect can be accomplished by reducing the number of proliferating tumor cells in the tumor (e.g., by reducing cell division of the tumor cells) and/or by inducing cytotoxicity or cell death (apoptosis) of existing tumor cells. Accordingly, tumor growth is arrested or prevented.

As used herein, the term "inhibiting cancer" or "inhibiting cancer cell growth" is intended to include the inhibition of undesirable or inappropriate cell growth. The inhibition is intended to include inhibition of proliferation including rapid proliferation. The term "inhibiting cancer cell growth" is also intended to encompass inhibiting tumor growth which includes the prevention of the growth of a tumor in a subject or a reduction in the growth of a pre-existing tumor in a subject. The inhibition also can be the inhibition of the metastasis of a tumor from one site to another. A cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

As used herein, "a," "an," "the," "at least one," and "one or more" are used interchangeably. Thus, for example, a pharmaceutical composition comprising "an" immune response modulator (IRM) compound can be interpreted to mean that the pharmaceutical composition includes at least one IRM compound.

As used herein, the term "subject" shall mean any animal including, without limitation, a human, a mouse, a rat, a rabbit, a non-human primate, or any other mammal. In one embodiment, the subject is a primate. In another embodiment, the subject is a human.

Also herein, the recitations of numerical ranges by endpoints include all numbers subsumed within that range (e.g., 1 to 5 includes 1, 1.5, 2, 2.75, 3, 3.80, 4, 5, etc.). Additionally, the inventive resiquimod containing compositions may contain between 0.1-0.5%

As used herein, the term "synergistic" refers to a combination of therapeutic agents described herein, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of the agent(s) to a subject with a disease or disorder, e.g., a proliferative disorder. The ability to utilize lower dosages of one or more therapeutic agent and/or to administer the therapeutic agent less frequently reduces the toxicity associated with the administration of the agent to a subject without reducing the efficacy of the therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone. As used herein, the term "in combination" refers to the use of more than one therapeutic agent. The use of the term "in combination" does not restrict the order in which the therapeutic agents are administered to a subject with a disease or disorder, e.g., a proliferative disorder. A first therapeutic agent, such as a compound described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer agent, to a subject with a disease or disorder, e.g. a proliferative disorder, such as cancer.

Immune response modifiers ("IRMs") include compounds that possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-alpha, IL-1, IL-6, IL-8, IL-0, IL-12, MIP-1, and/or MCP-1. As another example, certain IRM compounds can inhibit production and secretion of certain TH2 cytokines, such as IL-4 and IL-5. Additionally, some IRM compounds are said to suppress IL-1 and TNF (U.S. Pat. No. 6,518,265).

Resiquimod, (1-[4-amino-2-(ethoxymethyl)imidazo[4,5-c]quinolin-1-yl]-2-methylpropan-2-ol) is an immune response modifier (IRM) that works by stimulating cells through toll like receptors (TLR) 7 and 8.

As used herein, an "effective amount," when used with respect to the combination of agents described herein includes, without limitation, an amount of each agent in the combination that provides a statistically significant desired effect on cancer cells. In some embodiments, the effect amount can be narrowed to further require clinical acceptability of the amount of toxicity to non-cancer cells. Representative desired effects are described herein. For example, the effect can be a decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), a statistically significant increase in survival relative to treatment with individual agents of the combination or sub-combinations of the combination alone, and the like. The effective amount can vary depending on such factors as the type of cell growth being treated or inhibited, the type of therapeutic agent(s) employed, the particular therapeutic agent, the size of the subject, or the severity of the cancer cell growth or tumor. For example, the choice of each of the individual agents which make up the combination can affect what constitutes an "effective amount". One of ordinary skill in the art would be able to study the aforementioned factors and make the determination regarding the effective amount of the combination of the therapeutic agents without undue experimentation.

For example, an in vitro assay can be used to determine an "effective amount" of the therapeutic agents. The ordinarily skilled artisan would select an appropriate amount of each individual agent in the combination for use in the aforementioned in vitro assay. The cell survival fraction can be used to determine whether the selected amounts were an "effective amount" for the particular combination of therapeutic agents. For example, the selected amounts used within the assay preferably should result in a killing of at least 50% of the cells, more preferably 75%, and most preferably at least 95%. In a preferred embodiment, the effective dose of the therapeutic agent is a subtoxic dose. As used herein, the term subtoxic dose refers to a dose which results in the killing of less than about 10% of the cells.

The regimen (e.g., order) of administration can also affect what constitutes an effective amount. Further, several divided dosages, as well as staggered dosages, can be topically administered daily or sequentially, or the dose can be continuously infused. Further, the dosages can be proportionally increased or decreased as indicated by the exigencies of the therapeutic situation.

The phrase "pharmaceutically acceptable" is employed herein to refer to those combinations of therapeutic agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the therapeutic agents encompassed by the invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19)

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

Topical, Intracystic and Intratumoral Compositions Comprising Resiquimod for the Treatment of Diseases Chemical penetration enhancers are often used in topical and transdermal formulations to enhance the absorption, uptake and delivery of active pharmaceutical ingredients (drug or drug substance) into the skin. Such formulations may also be employed to complement further permeation within a localized compartment of the tissue and/or to enhance an immune-related response in the tissue in which they are delivered. Design of specific chemical enhancer formulations is not trivial but requires the comprehensive understanding of the effect of these agents on the skin permeability. It is indeed feasible to match the specific chemical enhancer formulation with the physicochemical properties of the drug to specifically enhance the permeation and uptake of the drug into the skin/tumor. Such formulations include, but are not limited to, a combination of one or more chemical enhancers; one or more solvents or vehicles that improve portioning of the drug and chemical enhancers into the skin/tumor; and a gelling agent or matrix for their incorporation as a topical or intratumoral formulation. Several exemplars of chemicals under each category have been previously disclosed in the literature. However, the specific combination in which each ingredient is employed so that they match the physicochemical properties of the drug and improve its skin penetration are neither trivial nor singularly dependent on the specific properties of the individual chemicals. It is important to note that the effect of each ingredient on skin/tumor is dependent of the concentration employed in the formulation and there are synergistic effects to be anticipated from their combination in a single formulation. These effects can be additive, positively synergistic, or negatively synergistic. This then implies that the kinetics of skin/tumor penetration and cumulative effects of the drug delivered into and across the skin/tumor from these formulations depends on the specific formulation employed. It follows, therefore, that the physiological and biological and therapeutic endpoints of the drug is determined to a large extent by the formulation in addition to the drug properties. These endpoints include, but are not limited to, the pharmacokinetics/pharmacodynamics (PK/PD), cumulative absorption as determined by the area under the curve (AUC), bioequivalence, therapeutic index (TI), to highlight a few. Furthermore, the specific formulation of the drug affects not only its potency but also the tolerance/safety on the skin on application. This can include, but is not limited to, adverse effects such as irritation, skin toxicity, erythema amongst others.

A beneficial effect of chemical permeation enhancers in addition to enhancing the permeation of a drug across a tissue, or within a localized tissue compartment such as a tumor, is to provide an inflammatory effect that is influential in directing the immune response important in tumor therapy. Incorporation of agents in topical, intracystic and/or injectable formulations can therefore achieve additive or more than additive effects towards the therapeutic endpoint of tumor treatment.

Formulations which are suitable for administration include creams, ointments, solutions, gels, lotions, pastes, patches, foams or spray formulations containing such carriers as are known in the art to be appropriate. Dosage forms for the topical, intracystic or intratumoral administration of resiquimod and other agents include powders, sprays, ointments, pastes, creams, ointments lotions, gels, solutions, and patches. The active component may be mixed under sterile conditions with a pharmaceutically-acceptable carrier, and with any preservatives, buffers, or propellants which may be required. The ointments, pastes, creams, lotions, solutions, foams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Injectable formulations may also be achieved by use of purified oils (soybean oil, safflower oil, triolein, and castor oil, fractionated coconut oil, miglyol810, 812, Neobee MS, Captex 300) and FDA approved dermal fillers (hydroxylapatite, hyaluronic acid, Poly-L-Lactic Acid, collagen, hydrogel) as components of injectable formulation.

Topical, intracystic and intratumoral formulations can be designed that are optimized by selecting the specific ingredients of the formulation including the enhancer, vehicle and the matrix (Karande 2004 Nature Biotechnology, Karande 2005 PNAS, and related references within and citing these works). Specific formulation can have a profound effect on efficacy of the drug and the target indication. We have established the physicochemical properties of resiquimod from its structure and chemical composition (http://pubchem.ncbi.nlm.gov/compound/Resiquimod #section=Depositor-Supplied-Synonyms). We have identified chemical descriptors for permeation enhancers that allow us to balance their potency and safety. Based on these we have identified combinations of chemical permeation enhancers that contain chemicals from the list below in the total concentration range of 0-2% wt/vol in weight fractions ranging between 0 and 100%. The formulation may contain 2 or 3 individual chemicals in a solvent to make the formulation. Resiquimod will be combined in such formulations.

Sodium octyl sulfate, Sodium decyl sulfate, Sodium dodecyl sulfate, Sodium tetradecyl sulfate, Sodium heptadecyl sulfate, Sodium eicosyl sulfate, Sodium laureth sulfate, Nicotine sulfate, Sodium taurocholic sulfate, Dimethyl sulfoxide, Sodium tridecyl phosphate, ChemBetaine CAS, ChemBetaine Oleyl, ChemBetaine C, Hexadecyldimethyl ammonio propane sulfonate, Decyldimethyl ammonio propane sulfonate, Dodecyldimethyl ammonio propane sulfonate, Myristyldimethyl ammonio propane sulfonate, Benzyl pyridinium chloride, Dodecyl pyridinium chloride, Cetyl pyridinium chloride, Benzyldimethyl dodecyl ammonium chloride, Benzyldimethyl myristyl ammonium chloride, Benzyldimethyl stearyl ammonium chloride Octyltrimethyl ammonium bromide, Decyltrimethyl ammonium bromide, Dodecyltrimethyl ammonium bromide, Myristyltrimethyl ammonium chloride, Cetyltrimethyl ammonium bromide Sorbitan monolaurate, Sorbitan monopalmitate, Sorbitan monostearate, Sorbitan monooleate Polyoxyethylene sorbitan monolaurate, Polyoxyethylene sorbitan monopalmitate, Brij 97 Brij 30, Brij 56, Triton X-100, Hexanoic acid, Octanoic acid, Decanoic acid, Undecanoic acid Dodecanoic acid, Tridecanoic acid, Myristic acid, Palmitic acid, Stearic acid, Oleic acid, Elaidic acid, Linoleic acid, Linolenic acid, Cholic acid, Methyl hexanoate, Ethyl undecanoate, Methyl laurate, Methyl tridecanoate, Methyl myristate, Isopropyl myristate, Isopropyl palmitate, Palmityl palmitate, Diethyl sebaccate, Tetracaine, Glyceryl monolaurate, Glyceryl monooleate Ethylpiperazine carboxylate, N-Lauryl sarcosinate, Sodium caprylate, Sodium decanoate, Sodium palmitate, Sodium oleate, Octyl amine, Decyl amine, Dodecyl amine, Tetradecyl amine, Oleyl amine, Urea, Methyl pyrrolidone, Cyclohexyl pyrrolidone, Octyl pyrrolidone, Decyl pyrrolidone, Decyl methyl pyrrolidone, Methyl piperazine, Phenyl piperazine, Octanamide Hexadecanamide, Caprolactam, Carveol, Pinene oxide, Limonene, Menthol, Pulegone, Carvacrol Pinene, Menthone, Terpineol, Cineole, Fenchone, Triacetin, Trimethoxy propylene methyl benzene, Linalool, Geraniol, and Octyl dodecanol. Others include sulfoxides, alcohols, polyols, alkanes, fatty acids, esters, amines and amides, terpenes, surface-active agents, cyclodextrins, $C_2$ or $C_3$ alcohols and higher, a $C_3$ or $C_4$ diol or higher, DMSO, DMF, DMA and related solvents, 1-n-dodecyl-cyclazacycloheptan-2-one, N-methyl-pyrrolidone and N-(2-hydroxyethyl)pyrrolidone, and a broader class of azones, and mixtures (binary, ternary or higher)

The physicochemical and structural properties of resiquimod indicate that it is a small molecule with reasonable hydrophobicity attributed by its aromatic nature. Chemical enhancers that improve transport of such molecules generally, but not exclusively, tend to be long chain hydrocarbons with a polar head group such as surfactants, fatty acids and fatty esters. Unsaturation (single or double) in the hydrocarbon chain can additionally aid the fluidization of skin lipid bilayers and permeation of resiquimod. Oleic acid, linoleic acid, linolinic acid, palmitic acid, myristic acid, etc. are exemplars of fatty acids. Esters of fatty acids such as palmitate, myristate, oleate, linoleate, etc. with a small alkyl group such as methyl, ethyl, propyl or butyl are examples of fatty esters. Salts of fatty esters such as sodium lauryl sulfate, sodium oleate, etc, are examples of surfactants. Short chain alcohols including ethanol, isopropanol, butanol, hexanol, etc. are examples of solvents. Combinations of chemicals and solvent can significantly enhance the permeation of resiquimod across skin. All potential combinations of such exemplars are viable formulations with varying potency and safety with varying PK/PD profiles for the API resiquimod.

Examples of formulations that embody the chemicals noted above and their combinations are as follows: Resiquimod concentration is 0.01, 0.02, 0.03, 0.04 to 1%, and can be combined with the components listed in i, ii, iii, iv, v, vi, vii, viii, ix, x, xi, xii or xiii.

i. Oleic acid (50%) and isopropyl myristate (50%) in a solution containing 50 ml phosphate buffered saline and 50 ml ethanol at a total concentration of 1% wt/vol.
ii. Isopropyl myristate (50%) and sodium lauryl sulfate (50%) in a solution containing 50 ml phosphate buffered saline and 50 ml ethanol at a total concentration of 0.5% wt/vol.
iii. Oleic acid (50%) and sodium lauryl sulfate (50%) in a solution containing 50 ml phosphate buffered saline and 50 ml ethanol at a total concentration of 0.5% wt/vol.
iv. Oleic acid (33%), isopropyl myristate (33%) and sodium lauryl sulfate (33%) in a solution containing 50 ml phosphate buffered saline and 50 ml ethanol at a total concentration of 0.5% wt/vol.
v. Isopropyl palmitate (50%) and sodium oleate (50%) in a solution containing 50 ml phosphate buffered saline and 50 ml ethanol at a total concentration of 2% wt/vol.
vi. Sodium lauryl sulfate (25%) and linoleic acid (75%) in a solution containing 50 ml phosphate buffered saline and 50 ml ethanol at a total concentration of 1.0% wt/vol.
vii. Palmitic acid (50%) and isopropyl laurate (50%) in a solution containing 50 ml phosphate buffered saline and 50 ml ethanol at a total concentration of 2.0% wt/vol.
viii. Oleic acid (50%) and linoleic acid (50%) in a solution containing 50 ml phosphate buffered saline and 50 ml ethanol at a total concentration of 1.5% wt/vol.
ix. Linoleic acid (25%), oleic acid (25%) and isopropyl linoleate (50%) in a solution containing 50 ml phosphate buffered saline and 50 ml ethanol at a total concentration of 0.5% wt/vol.
x. Sodium oleate (33%), oleic acid (33%) and methyl palmitate (33%) in a solution containing 50 ml phosphate buffered saline and 50 ml ethanol at a total concentration of 2.0% wt/vol.

xi. A solution containing 50 ml phosphate buffered saline and 50 ml ethanol.

xii. Oleic acid (10%) in a solution containing 50 ml phosphate buffered saline and 50 ml ethanol.

xiii. Oleic acid (2%) and sodium lauryl sulfate (5%) in a solution containing 50 ml phosphate buffered saline and 50 ml ethanol.

The following example is provided to illustrate certain embodiments of the invention. It is not intended to limit the invention in any way.

EXAMPLE I

Topically Applied Resiquimod Inhibits the Progression of Precancerous and Cancerous Lesions A majority of nevi and melanomas contain BRAF mutations, particularly the BRAFV600E mutation. To test whether resiquimod can be used to treat cutaneous diseases that have the potential to become malignant tumors and early stage malignant tumors, we tested the treatment efficacy of resiquimod on skin tumors using four different mouse models: 1) a Tyr:creER, BrafCa nevus model in which the mice develop nevus like lesions including atypical proliferation of melanocytes in the epidermis (atypical intraepidermal melanocytic proliferation), 2) a Tyr::CreER, Phd2lox/lox, BRafCA melanoma model in which these mice will develop primary melanoma were selected 3) Tyr::creER, BRAF$^{ca}$, $^{Pten lox/lox}$ a melanoma model where the tumors develop very quickly, and 4) the B16 melanoma model.

In the genetically engineered mouse (GEM) models described above TLR activation induced changes were assessed. In the GEM models, tumors arise de novo in the context of a normal immune system and co-evolve with surrounding stroma. In addition, in situ melanoma can only be observed and studied in GEM models but not in the xenograft tumor models.

Effect of Resiquimod on Pigmented Tumor Progression in Tyr::creER, BRAF$^{ca}$ mice.

We first tested treatment efficacy of resiquimod in Tyr::creER, BRAF$^{ca}$ mice. This formulation comprised 0.2% resiquimod, propylene glycol, colloidal silicon dioxide, and triacetin. These mice develop nevus-like pigmented tumors after 4-HT induction, but lymph node metastasis does not occur. Mice treated with blank topical gel were used as controls. When pigmented lesions became palpable in Tyr::creER, BRAF$^{ca}$ mice, we treated these mice with topical resiquimod or blank gel twice a week for six weeks (FIG. 1A). Tumor diameters were measured using calipers every three days. The pigmented tumors in the control group continued to grow (FIGS. 1B and 1I), while the pigmented lesions treated with resiquimod regressed (FIGS. 1C and 1I). Histological examination showed that pigmented tumor cells occupied the dermis in the control mice (FIG. 1F), while the tumor cells in mice treated with resiquimod disappeared and only many macrophages with pigment can be seen in the dermis (FIG. 1G). Pigmented tumor cells in the epidermis also regressed completely (data not shown). In a different experiment, we waited until the pigmented lesions became palpable (FIG. 1D), then we treated these mice with topical resiquimod for 1 month. The same pigmented lesion disappeared after treatment (FIG. 1E). These mice were sacrificed and histology showed only pigment containing macrophages in the dermis and viable tumor cells were not seen.

Effect of Resiquimod on Melanoma Progression in Tyr::creER, BRAF$^{ca}$, Phd2$^{lox/lox}$ Mice.

The Tyr:creER, BRAF$^{ca}$, phd2$^{lox/lox}$ mouse melanoma model was developed in Dr. Xu's lab. Melanoma can be induced with 100% penetrance using topical 4-HT. Lymph node metastasis is frequent in these mice. However, unlike the Tyr::creER, BRAF$^{ca}$, Pten$^{lox/lox}$ mice, the latency of melanoma development is significantly longer and the median survival after Cre activation is about 180 days instead of 60 days in Tyr::creER, BRAF$^{ca}$, Pten$^{lox/lox}$ mice. Once these mice developed palpable tumor (140 days after induction), we started topical resiquimod treatment (0.2%) twice a week for 6 weeks (FIG. 2A). The melanoma in control mice grew and the tumor became very big at day 180 (FIG. 2B). These mice were sacrificed. The underside of skin was occupied completely by tumor (FIG. 2C). Histologically, the dermis was filled entirely by melanoma cells (FIG. 2D and FIG. 2E). In contrast, melanoma growth was inhibited after resiquimod treatment (FIG. 2F). The underside of skin had significantly less tumors (FIG. 2G). Histologically, dermal melanoma had regressed (FIG. 2H) and numerous macrophages with pigment were present in the dermis (FIG. 2I), indicating melanoma has regressed. None of the treated mice developed lymph node metastasis. In the periphery of melanoma in the control mice, melanoma cells were seen in the epidermis (FIG. 2K) and they disappeared after treatment (FIG. 2I).

Figures 3B, 3C:
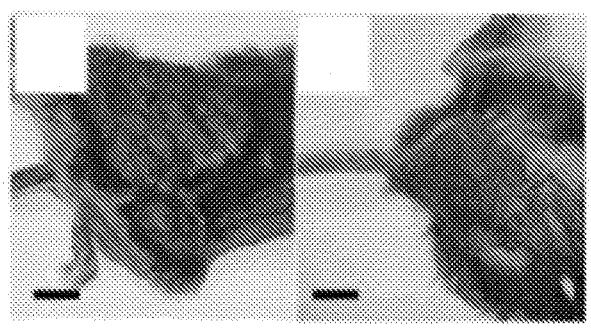
Figure 3F:
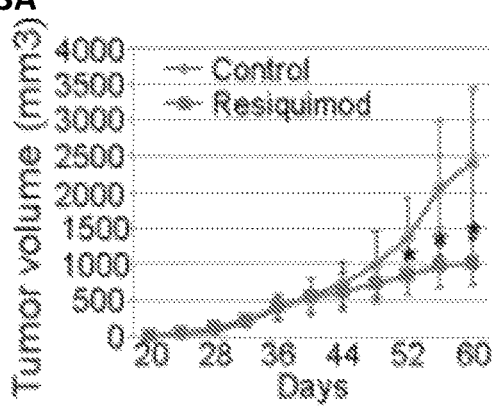
Figures 3D, 3E:
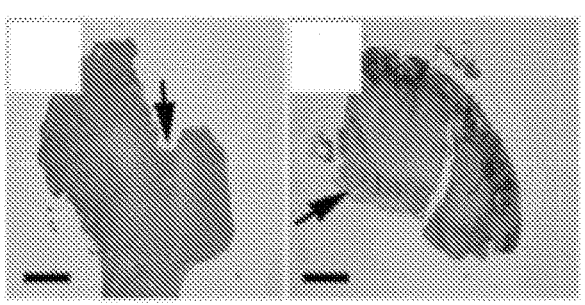
Figure 3G:
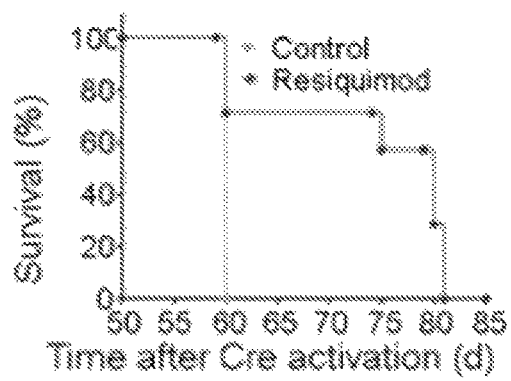
Figure 3H:
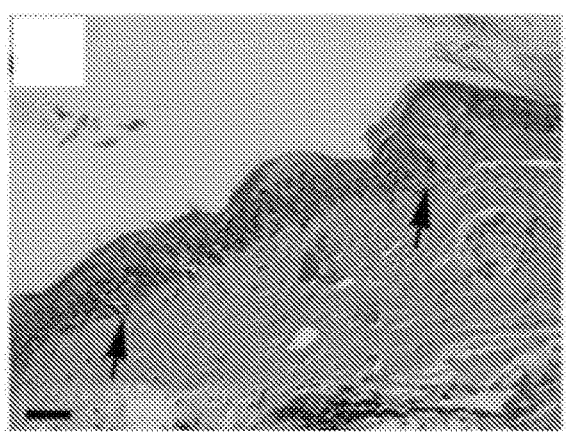
Figure 3I:
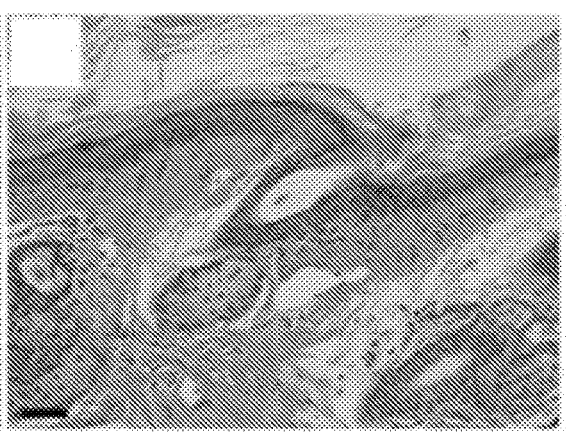

Effect of Resiquimod on Melanoma Progression in Tyr::creER, BRAF$^{ca}$, Pten$^{lox/lox}$ Mice Because melanoma in Tyr::creER, BRAF$^{ca}$, Phd2$^{lox/lox}$ mice has long latency and melanoma growth is relatively slow, we next tested resiquimod gel in Tyr::creER, BRAF$^{ca}$, Pten$^{lox/lox}$ mice, in which melanoma grows much faster. Once these mice developed palpable tumors, we treated the mice with resiquimod twice a week for 6 weeks (FIG. 3A). The mice treated with control vehicle developed bulky tumors (FIGS. 3B and 3F). Resiquimod treatment significantly slowed melanoma growth (FIGS. 3C and 3F). Furthermore, resiquimod treatment prolonged the lifespan of the treated mice (FIG. 3G). Histologically, melanoma infiltrated through the panniculus carnosus muscle in the control mice (FIG. 3D); while melanoma was thinner and did not infiltrate through the skeletal muscle in the resiquimod treated mice (FIG. 3E). In the periphery of melanoma in the control mice, in situ melanoma was seen in the epidermis (FIG. 3H) and they disappeared after treatment (FIG. 3I).

In another experiment, mice were treated with control vehicle or resiquimod for 3 weeks and then sacrificed while they were still on the treatment (FIG. 4A). All 5 mice in the control group developed lymph node metastasis and the number of positive lymph nodes ranged from 2-4 per mouse (FIG. 4B), while in the resiquimod treated group 2 of 5 mice developed lymph node metastasis and 1 positive node each was identified in these mice (FIG. 4B). The treated mice had significantly thinner tumors (FIG. 4C). Tumor and spleen tissues were processed and multicolor flow cytometry analysis was performed. Our analysis detected a significant increase of CD45$^+$ inflammatory cells (FIG. 4D) and decrease of CD45$^+$CD11B$^+$F4/80$^-$Ly6g$^{high}$ MDSCs in the tumor after treatment (FIG. 4E). The expression of granzyme B increased in CD8$^-$ T cells (FIG. 4F); the number of GranB$^+$CD8$^+$ and GranB$^+$CD8$^+$Ki-67$^+$ T cells were increased after resiquimod treatment (FIGS. 4G and 4H) indicating effector T cell activation. Interestingly, PD1$^+$CD8$^+$ T cells were also significantly increased, suggesting an expanded tumor recognizing T cell repertoire. Data from spleen are similar to these in the tumor (data not shown).

Effect of Resiquimod on Melanoma Progression in the B16 Melanoma Model

Figure 5A:
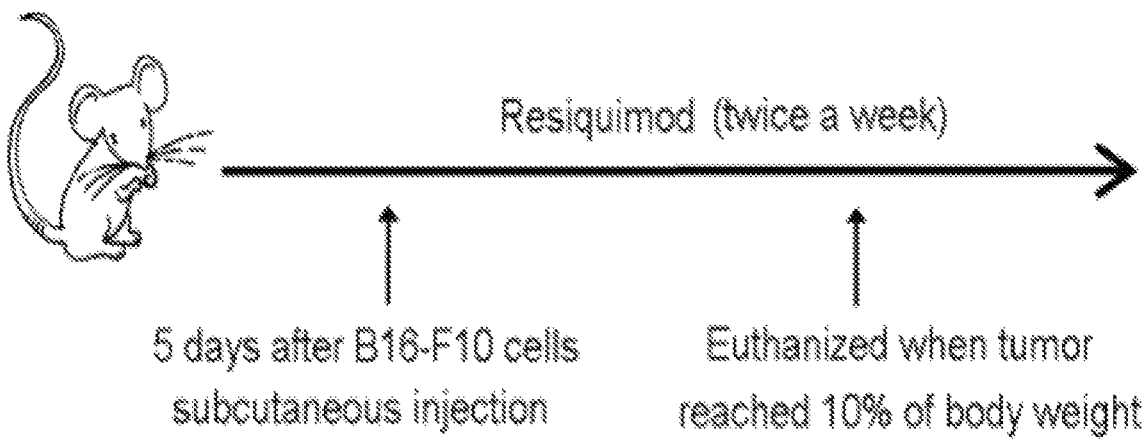
FIGS. 5A-5E. Resiquimod inhibits melanoma growth in B16 melanoma model.
Figure 5B:
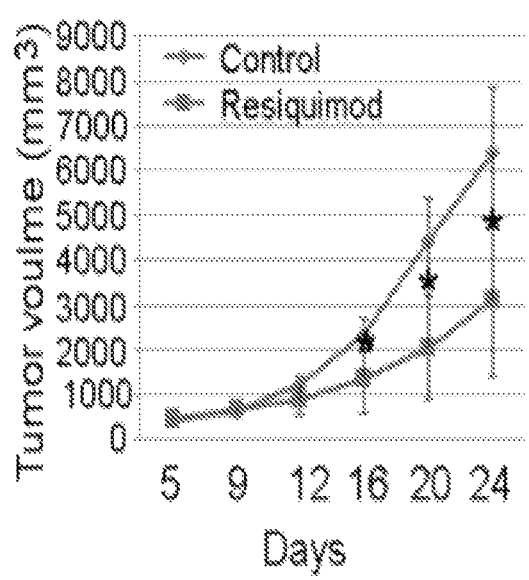
Figure 5C:
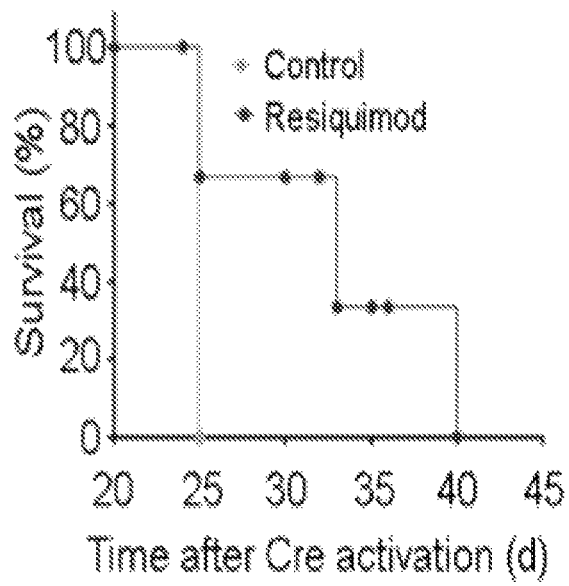
Figure 5D:
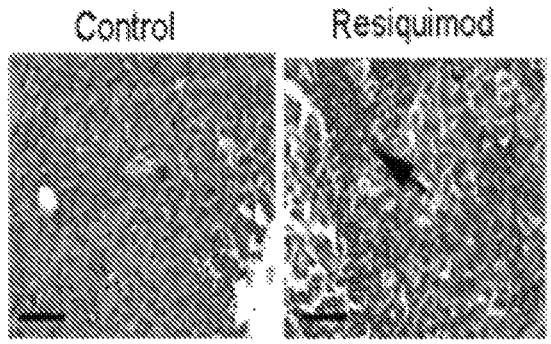
Figure 5E:
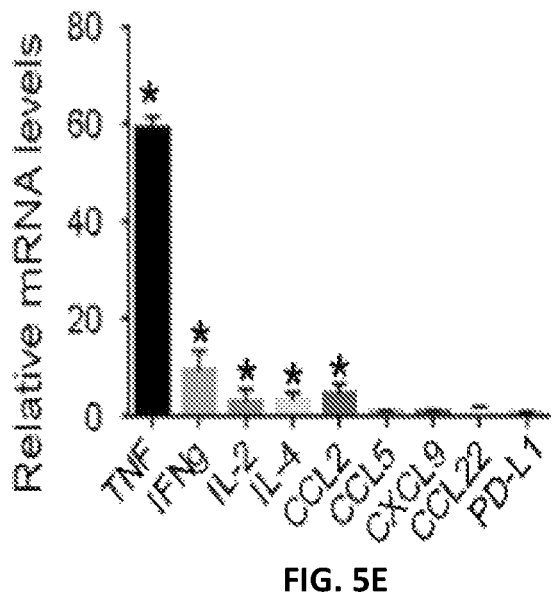

To study whether the effect of resiquimod depends on BRAF mutation, we tested the 0.2% resiquimod gel in C57BL/6J mice with the B16-F10 melanoma cells. Once these mice developed palpable tumors, we started resiquimod treatment twice a week (FIG. 5A). Resiquimod treatment significantly slowed the melanoma growth (FIG. 5B) and prolonged the lifespan of the treated mice (FIG. 5C). Histology showed more inflammatory cells in the tumor after resiquimod treatment (FIG. 5D). Tumor tissues were processed and we measured cytokine and chemokine mRNA expression in the tumor using qRT-PCR. The analysis showed increased TNF-α, INF-γ and CCL2 expression after resiquimod treatment compared to levels in control mice (FIG. 5E).

Effect of Resiquimod on Melanoma Progression is Mediated through CD8+ T Cells

Figure 6A:
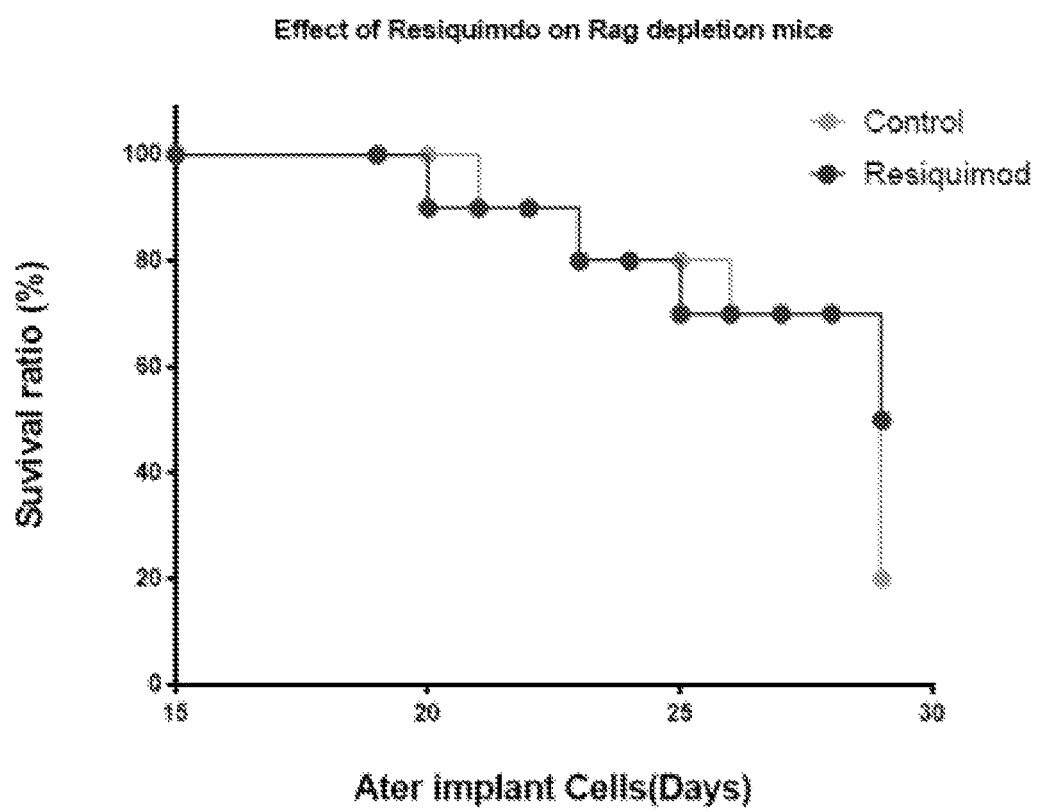
FIGS. 6A-6C. CD8+ T cells mediate the effect of resiquimod on melanoma.
Figure 6B:
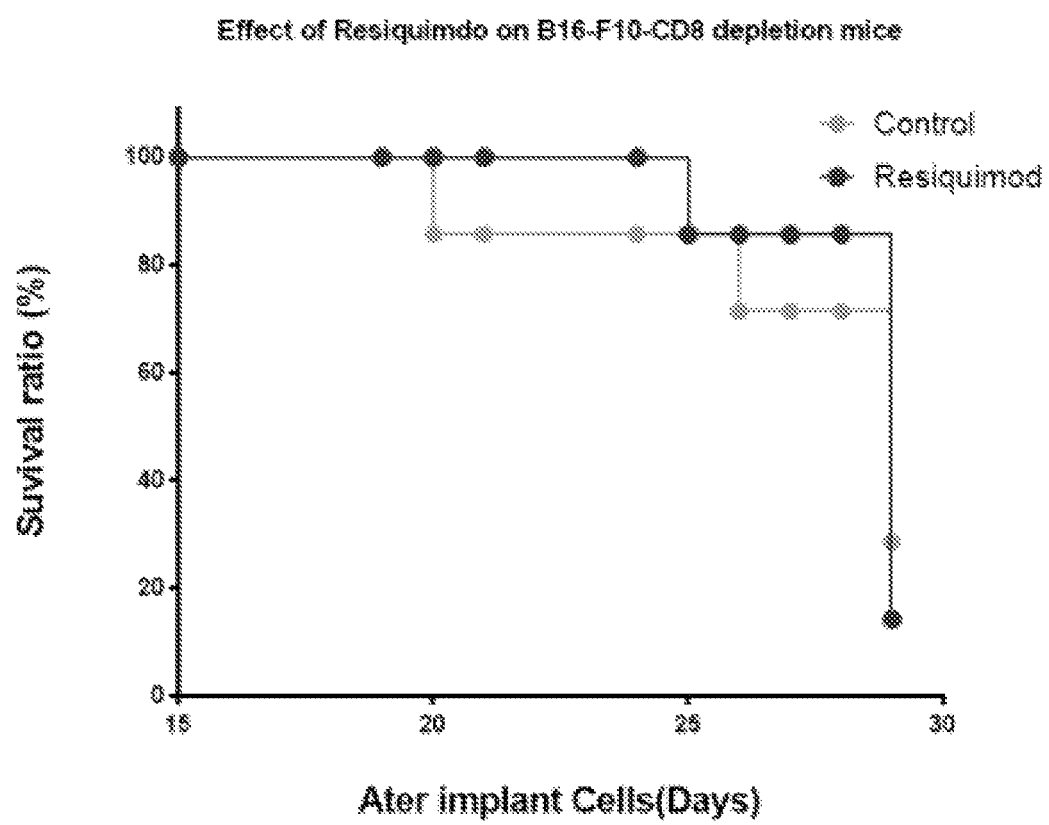
Figure 6C:
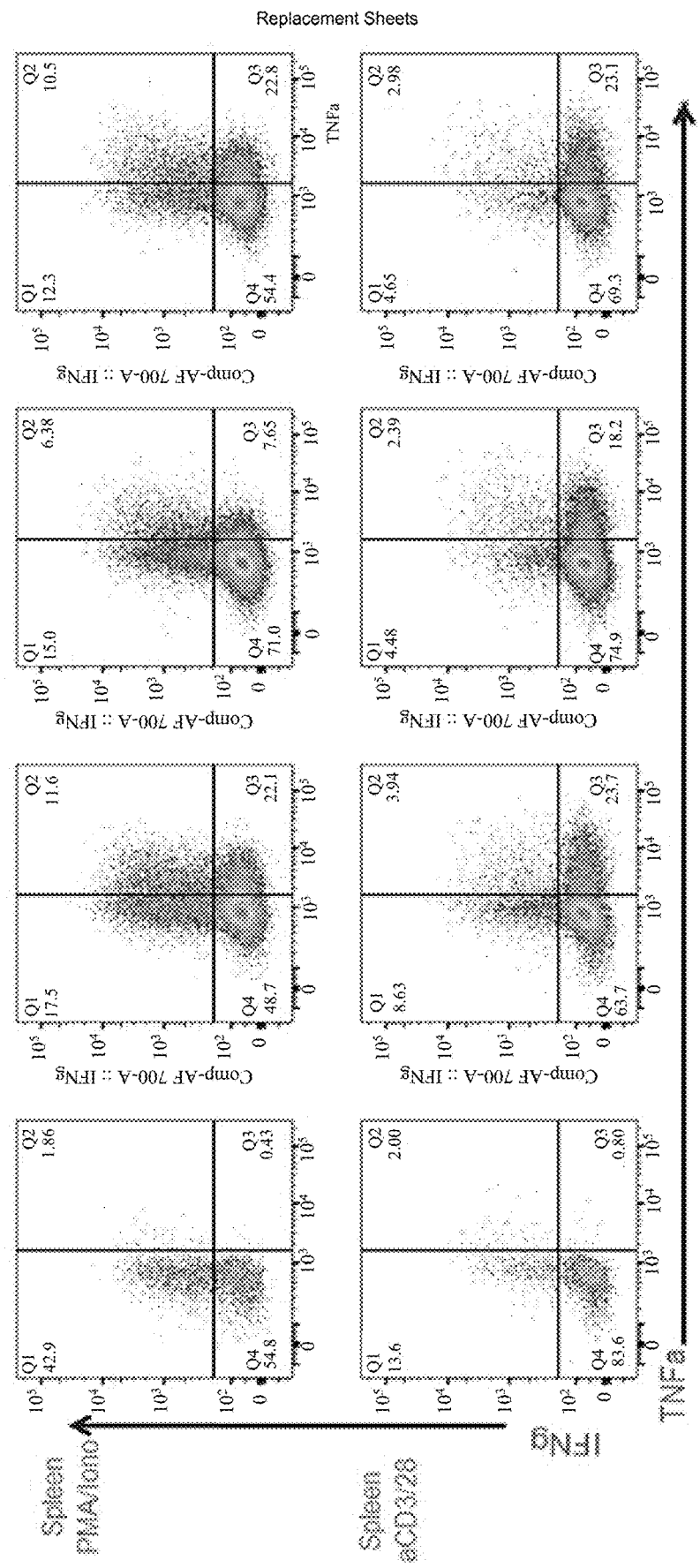

To study whether the effect of resiquimod depends on T cells, the effects of resiquimod gel in RAG-1-deficient mice using B16-F10 melanoma cells were tested. RAG-1-deficient mice do not have mature B and T lymphocytes. Once these mice developed palpable tumors, resiquimod treatment was administered twice a week. Resiquimod treatment had little effect on melanoma growth (FIG. 6A). To study whether the effect of resiquimod depends on CD8+ T cells, we tested the effect of resiquimod gel in CD8 depleted C57 mice using B16-F10 melanoma cells. CD8 depletion was achieved using anti-CD8 antibody. Once these mice developed palpable tumors, resiquimod was administered twice a week. Resiquimod treatment had little effect on melanoma in CD8 T cell depleted mice, indicating that the effect is mediated through CD8 T cells (FIG. 6B). Resiquimod also has effects on cytokine release from T cells. Resiquimod treated T cells from spleen showed increased expression of IFN-γ after stimulation (FIG. 6C).

Combination of Resiquimod with anti-PD1 Therapy.

The efficacy of 0.2% resiquimod in combination with anti-PD1 in Tyr::creER, BRAF$^{ca}$, Pten$^{lox/lox}$ mice was assessed. Once these mice developed palpable tumors, they were treated the mice with resiquimod (twice a week for 6 weeks) and anti-PD1 therapy (200 μg, i.p., twice a week for 5 weeks, FIG. 7A). The mice treated with control vehicle developed bulky tumor (FIG. 7B) and the mice treated with anti-PD antibody also developed bulky tumors (FIG. 7C). Resiquimod treatment significantly slowed melanoma growth (FIG. 7D) and the combination therapy showed the most significant efficacy (FIG. 7E). The tumor volume was measured and shown in FIG. 7F. Anti-PD1 therapy alone had no effect on lymph node metastasis, while resiquimod significantly reduced the number of positive lymph nodes and the combination further decreased positive lymph nodes (FIG. 7G)

Enhanced Delivery of Resiquimod in Presence of Chemical Permeation Enhancers.

Figure 8A:
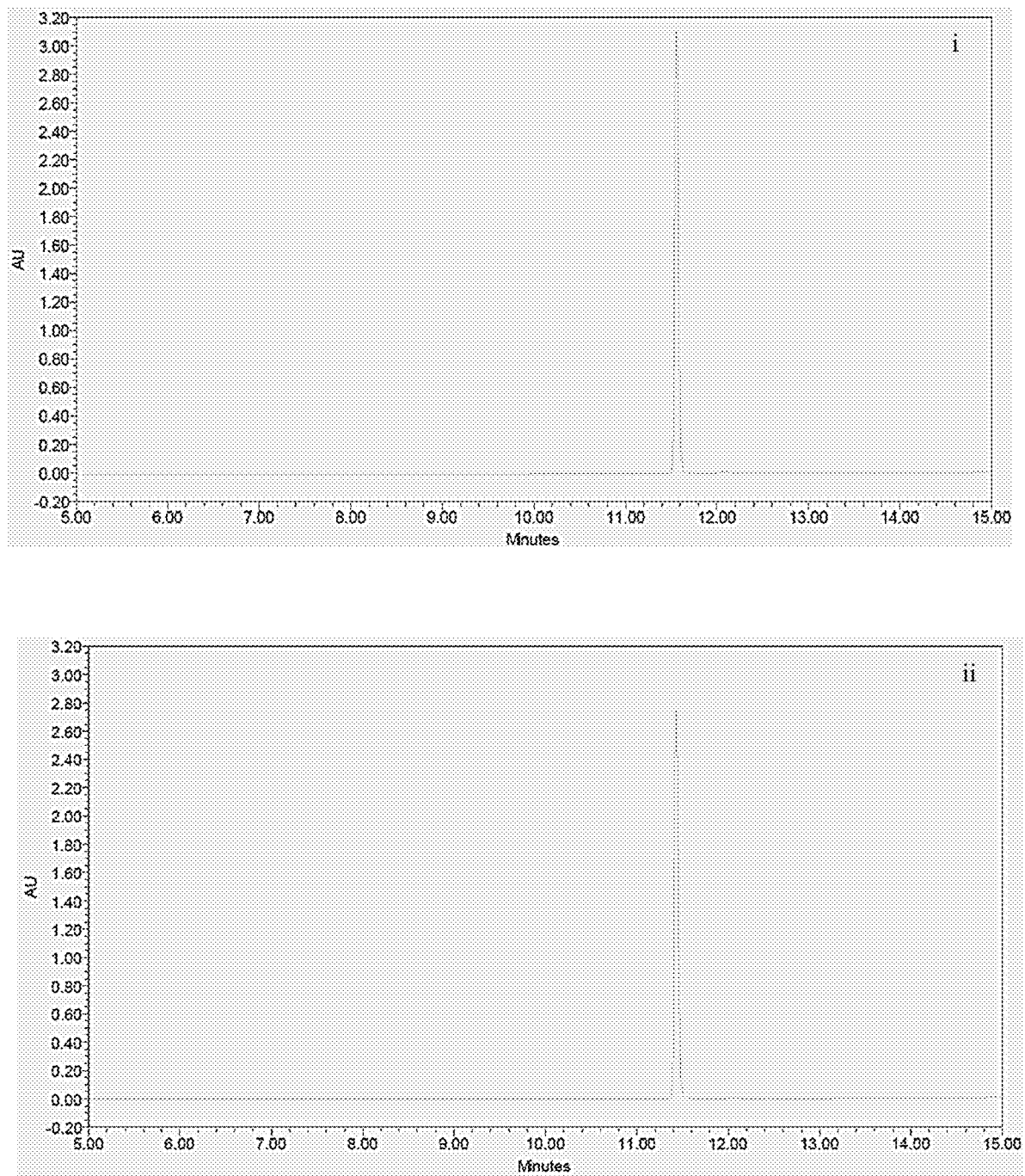
Figure 8C:
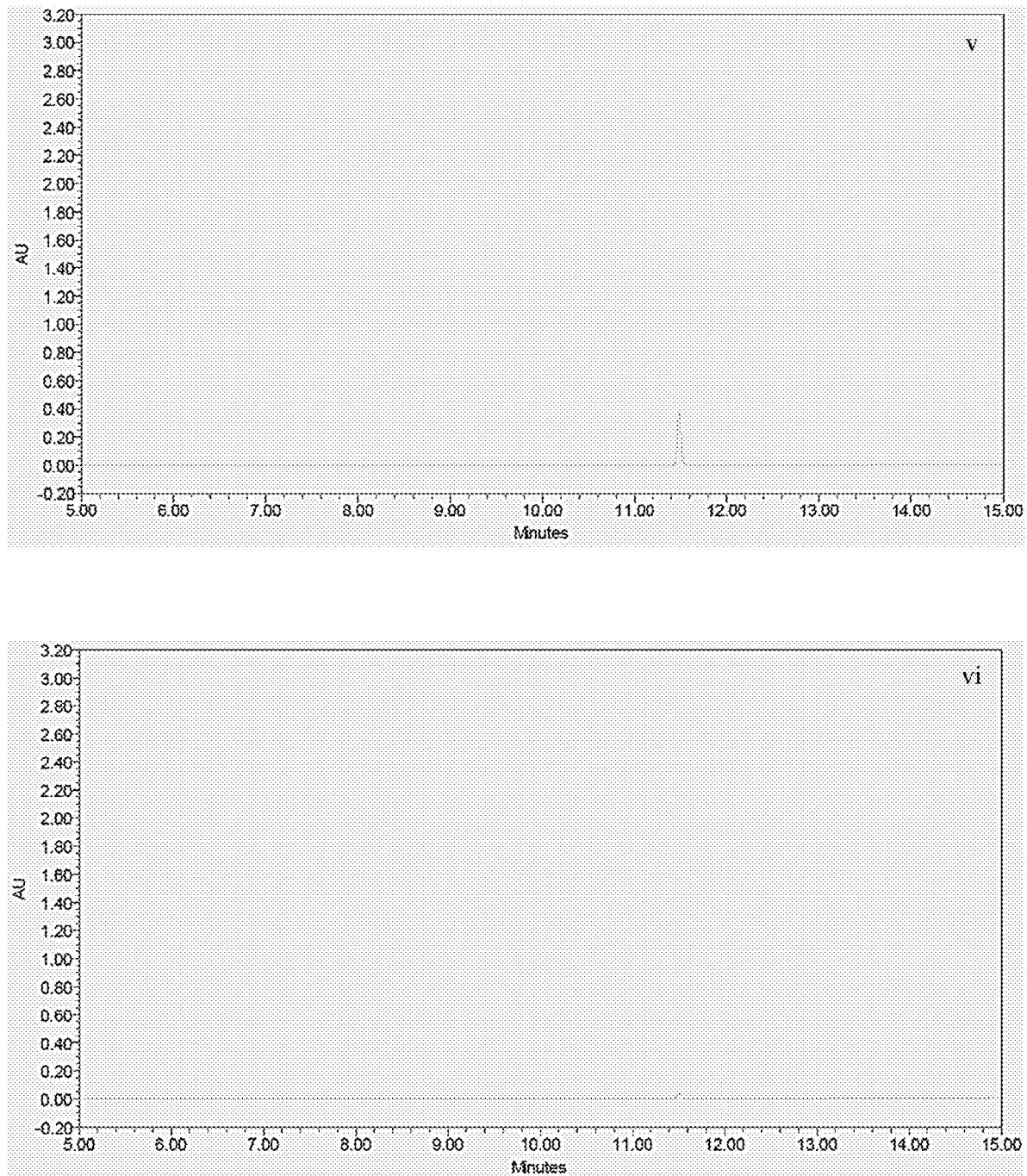
Figure 8D:
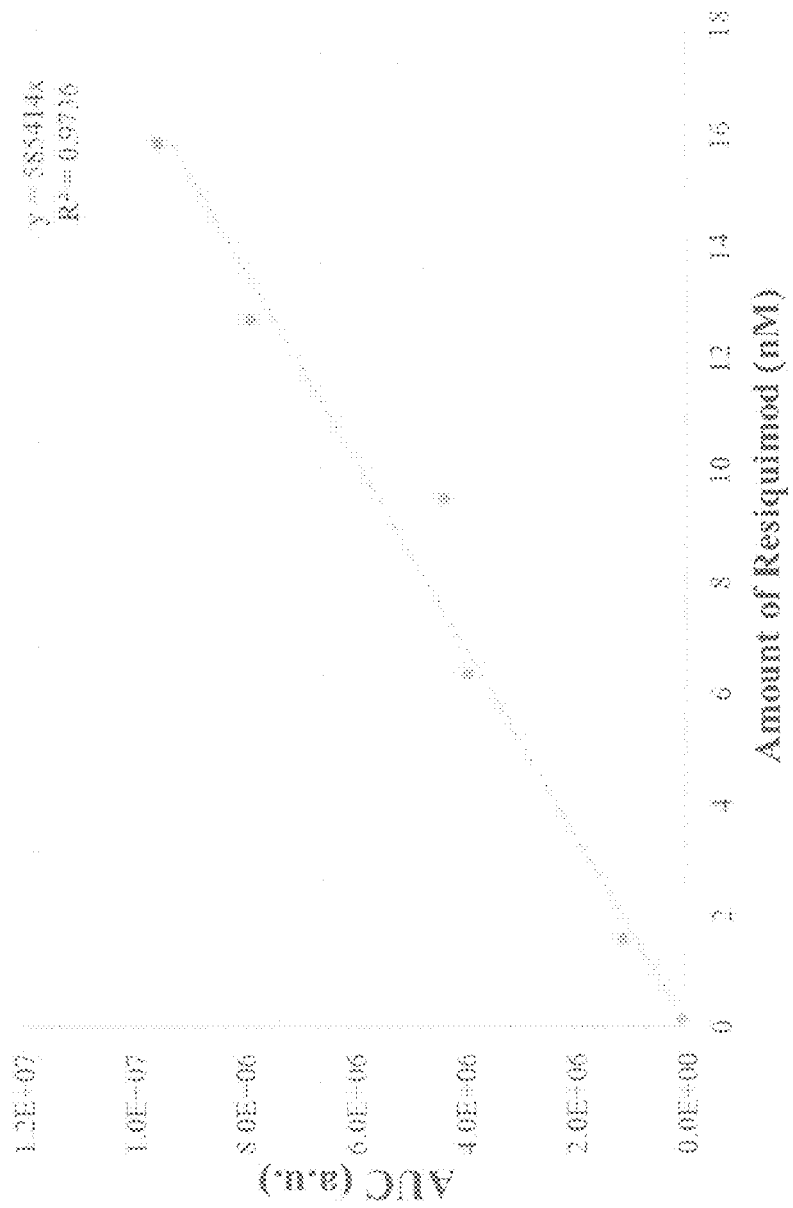
Figure 9A:
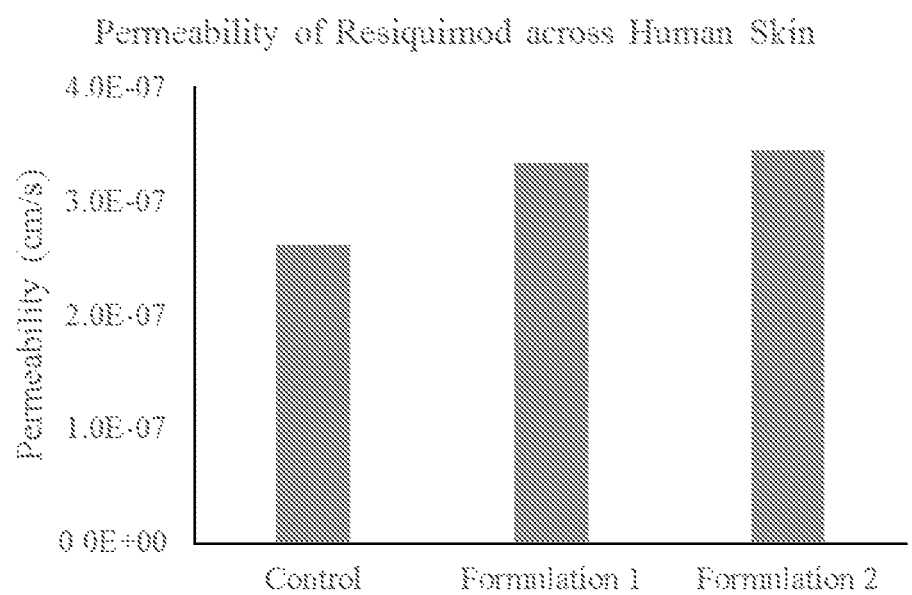
FIGS. 9A-9D. Enhanced delivery of resiquimod from topical formulations containing chemical permeation enhancers.
Figure 9B:
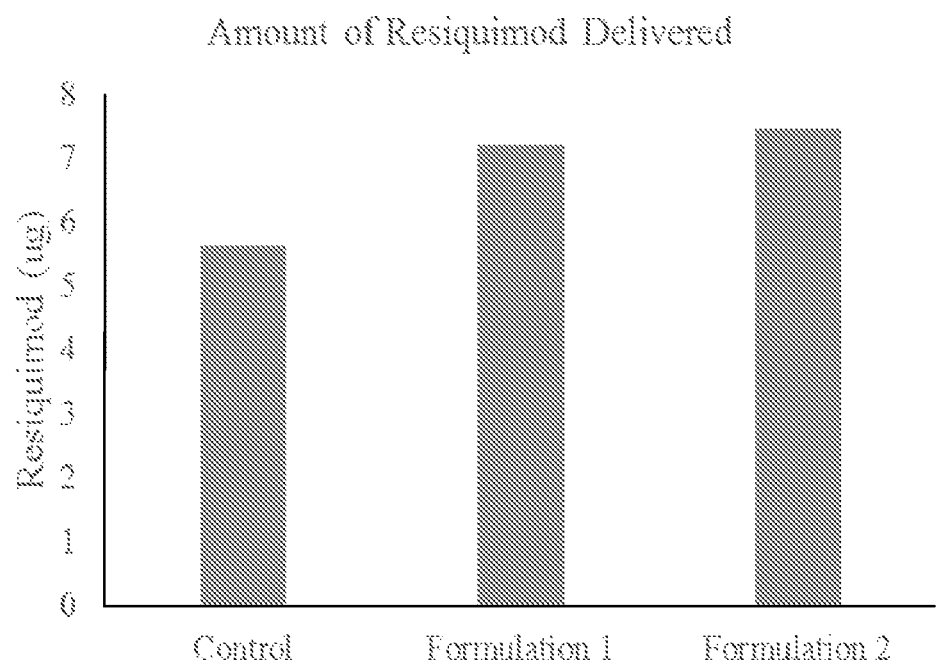
Figure 9C:
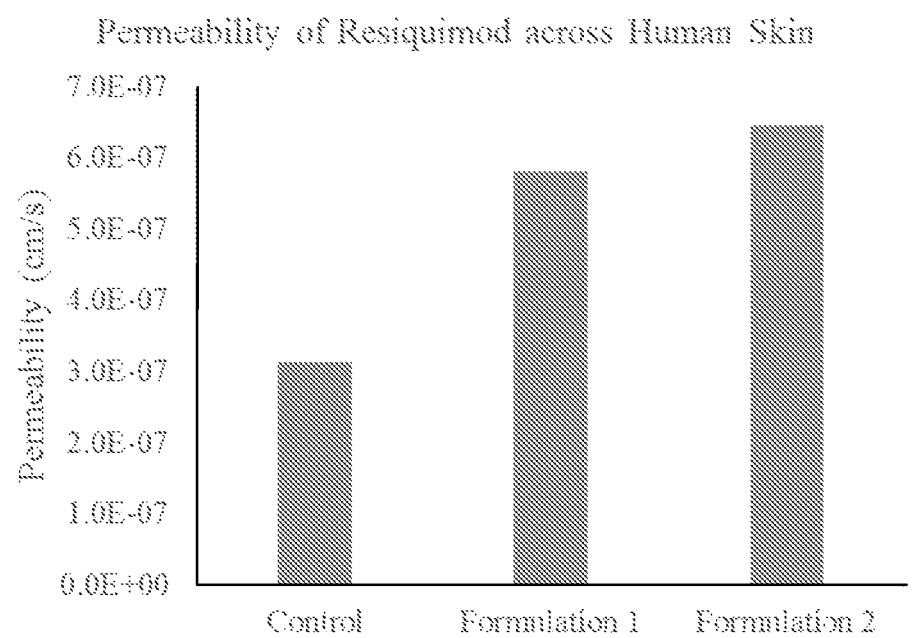
Figure 9D:
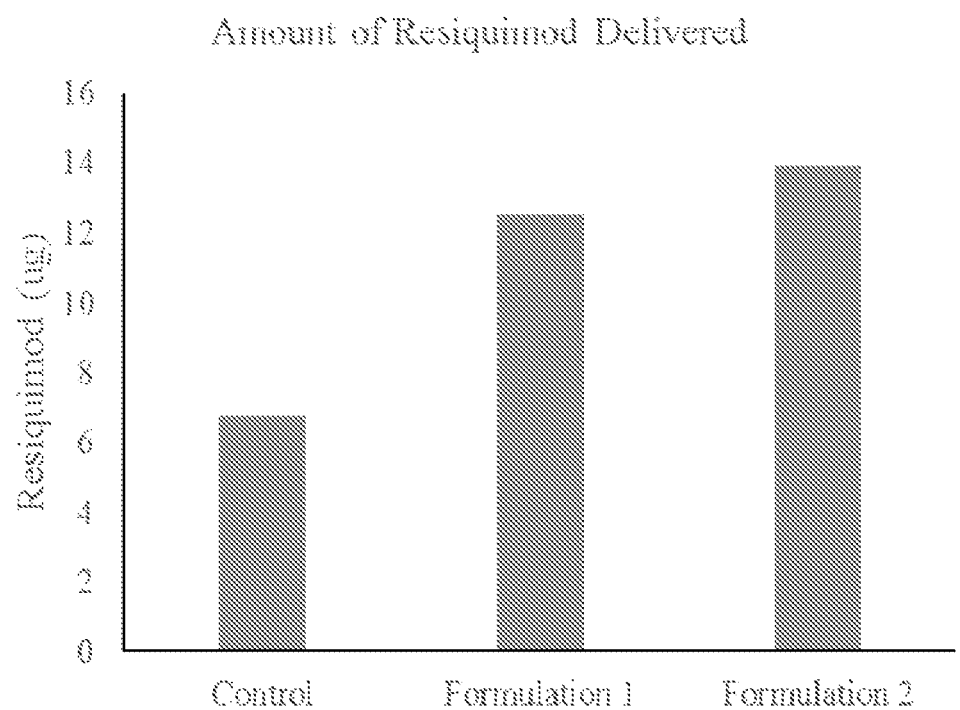

0.2% resiquimod permeation was determined for three different formulations across human skin. FIG. 8 shows the solubility and stability of resiquimod in the base formulation on 50:50 ethanol: PBS. Additionally, data in FIG. 9 show the enhanced permeation of resiquimod from formulations containing skin permeation enhancers. Chemical permeation enhancers are capable of reducing the lag time of permeation of resiquimod across human skin as well as increase the total amount of resiquimod delivered across human skin.

Adjuvancy Potency of Chemical Enhancer Formulations

Figure 10:
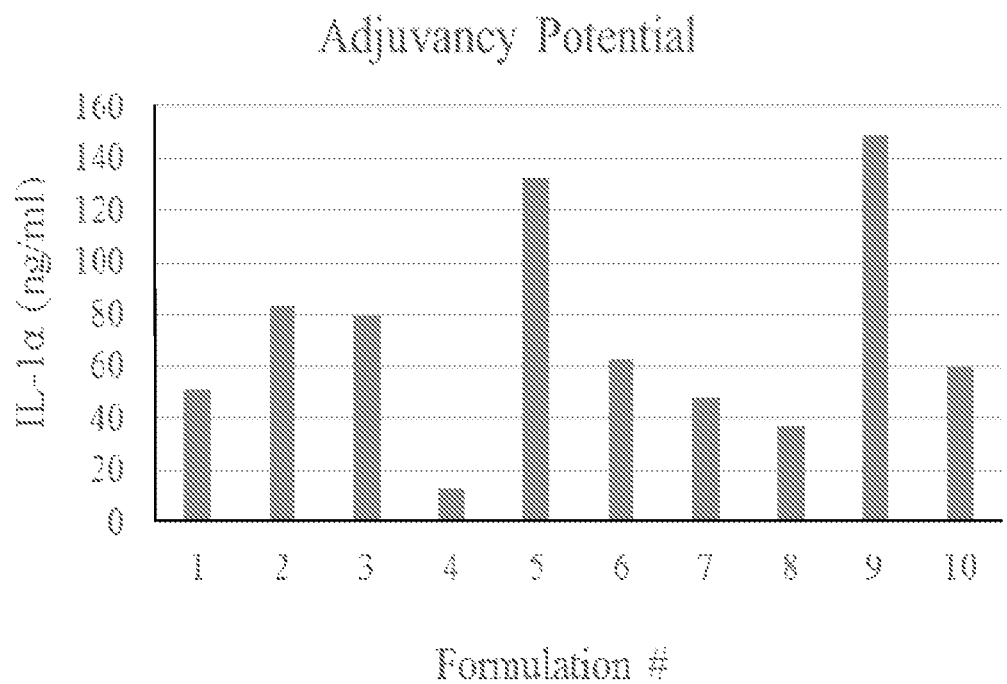

Immune stimulating capacity of test formulations was evaluated in terms of release of interleukin 1α (IL-1α) in an in vitro skin model EpiDerm™, a 3D cell culture of human normal epidermal keratinocytes after exposure to the formulations. To study the adjuvancy potential of test formulations on skin, cell cultures were exposed to 10 μL of the test formulation for 4 h. Each test formulation was analyzed in duplicate. Post exposure, the incubation medium was removed and stored at –° C. Cytokine content, specifically IL-1α, was measured using standard human colorimetric ELISA kits for IL-1α. The optical absorbance data from the extracted samples were then used, along with the standards, to determine the IL-1α released (ng/ml). Triton X100 (1% wt./vol.) was used as the positive control and 1:1 PBS:EtOH was used as the negative control. Data in FIG. 10 shows adjuvancy potential of 10 unique formulations tested. Formulations were designed as described previously.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for the treatment of tumors consisting of
   a) intratumorally injecting a formulation of between 0.01%-1% resiquimod, and a filler; and
   b) systemic administration of an anti-PD1 antibody,
      wherein said tumor is selected from melanoma, metastatic epithelial cancer, squamous cell carcinoma, basal cell carcinoma, lung, bladder, prostate, brain, breast, pancreas, ovary, liver, stomach, mesenchymal malignant tumor, sarcoma, and B cell lymphoma.

2. The method of claim 1, wherein intratumorally injecting the formulation of between 0.01%-1% resiquimod is to subcutaneous or internal tumors.

3. The method of claim 1, wherein the subcutaneous or internal tumors are secondary metastatic tumors.

4. The method of claim 1, wherein said tumor is melanoma.

5. The method of claim 1, wherein said tumor is squamous cell carcinoma.

6. A method for the treatment of tumors consisting of intratumorally injecting a formulation of between 0.01%-1% resiquimod; and a filler and applying local radiation to the tumor, wherein said tumor is selected from melanoma, metastatic epithelial cancer, squamous cell carcinoma, basal cell carcinoma, lung, bladder, prostate, brain, breast, pancreas, ovary, liver, stomach, mesenchymal malignant tumor, sarcoma, and B cell lymphoma.

7. The method of claim 6, wherein said tumor is melanoma.

8. The method of claim 6, wherein said tumor is squamous cell carcinoma.

9. The method of claim 6, wherein intratumorally injecting the formulation of between 0.01%-1% resiquimod is to subcutaneous or internal tumors.

10. The method of claim 1, wherein said filler is a dermal filler.

11. The method of claim 10, wherein said dermal filler is at least one of hydroxylapatite, Sodium hyaluronate, Poly-L-Lactic Acid, collagen, or hydrogel.

12. The method of claim 1, wherein said filler is a purified oil.

13. The method of claim 12, wherein said purified oil is at least one of soybean oil, safflower oil, triolein, castor oil, fractionated coconut oil, miglyol 810, miglyol 812, Neobee MS or Captex 300.

14. The method of claim 1, wherein said formulation is buffered.

15. The method of claim 6, wherein said filler is a dermal filler.

16. The method of claim 15, wherein said dermal filler is at least one of hydroxylapatite, sodium hyaluronate, Poly-L-Lactic Acid, collagen, or hydrogel.

17. The method of claim 6, wherein said filler is a purified oil.

18. The method of claim 17, wherein said purified oil is at least one of soybean oil, safflower oil, triolein, castor oil, fractionated coconut oil, miglyol 810, miglyol 812, Neobee MS or Captex 300.

19. The method of claim 6, wherein said formulation is buffered.

\* \* \* \* \*